US012195432B2

(12) United States Patent
Banister et al.

(10) Patent No.: US 12,195,432 B2
(45) Date of Patent: *Jan. 14, 2025

(54) 2-ARYLBENZIMIDAZOLES AS PPARGC1A ACTIVATORS FOR TREATING NEURODEGENERATIVE DISEASES

(71) Applicant: THE BOARD OF TRUSTEES OF THE LELAND STANFORD JUNIOR UNIVERSITY, Stanford, CA (US)

(72) Inventors: Samuel D. Banister, Castle Hill (AU); Edgar Engleman, Redwood City, CA (US); Khoa D. Nguyen, Redwood City, CA (US); Mark Smith, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 822 days.

This patent is subject to a terminal disclaimer.

(21) Appl. No.: 17/266,433

(22) PCT Filed: Aug. 6, 2019

(86) PCT No.: PCT/US2019/045229
§ 371 (c)(1),
(2) Date: Feb. 5, 2021

(87) PCT Pub. No.: WO2020/033359
PCT Pub. Date: Feb. 13, 2020

(65) Prior Publication Data
US 2021/0300877 A1 Sep. 30, 2021

Related U.S. Application Data

(60) Provisional application No. 62/714,962, filed on Aug. 6, 2018.

(51) Int. Cl.
C07D 235/08 (2006.01)
C07D 235/18 (2006.01)
C07D 263/57 (2006.01)
C07D 277/66 (2006.01)
C07D 401/04 (2006.01)
C07D 417/04 (2006.01)
C07D 471/04 (2006.01)
C07D 487/04 (2006.01)
C07F 9/6506 (2006.01)

(52) U.S. Cl.
CPC ......... C07D 235/08 (2013.01); C07D 235/18 (2013.01); C07D 263/57 (2013.01); C07D 277/66 (2013.01); C07D 401/04 (2013.01); C07D 417/04 (2013.01); C07D 471/04 (2013.01); C07D 487/04 (2013.01); C07F 9/65068 (2013.01); C07B 2200/05 (2013.01)

(58) Field of Classification Search
CPC .. C07D 235/18; C07D 263/57; C07D 277/66; C07D 401/04; C07D 417/04; C07D 471/04; C07D 487/04; C07F 9/65068; C07B 2200/05
See application file for complete search history.

(56) References Cited

U.S. PATENT DOCUMENTS

| 3,335,052 A | 8/1967 | Brown |
| 4,038,396 A | 7/1977 | Shen et al. |
| 4,188,486 A | 2/1980 | Tsukamoto et al. |
| 5,552,426 A | 9/1996 | Lunn et al. |
| 7,781,596 B1 | 8/2010 | Lubisch et al. |
| 7,893,271 B2 | 2/2011 | Chassaing |
| 7,915,299 B2 | 3/2011 | Petersen et al. |
| 8,803,921 B2 | 8/2014 | Kojo et al. |
| 9,120,711 B2 | 9/2015 | Nolan et al. |

(Continued)

FOREIGN PATENT DOCUMENTS

| CN | 104873500 A | 9/2015 |
| DE | 3830060 A1 | 3/1990 |

(Continued)

OTHER PUBLICATIONS

J. Lu, et al. Palladium-Catalyzed Synthesis of Aromatic Ketones and Isoindolobenzimidazoles via Selective Aromatic C—H Bond Acylation. Adv. Synth. Catal., 2013, 355: 529-536. https://doi.org/10.1002/adsc.201200743. (Year: 2013).*

K. Muto et al. (C—H arylation and alkenylation of imidazoles by nickel catalysis: solvent-accelerated imidazole C—H activation, Chem. Sci, 2015, VL-6, IS-12, p. 6792-6798, DO-10.1039/C5SC02942B. (Year: 2015).*

H. Chen et al. (External Oxidant-Free Regioselective Cross Dehydrogenative Coupling of 2-Aryl imidazoheterocycles and Azoles with H2 Evolution via Photoredox Catalysis, Adv. Synth. Catal. Jun. 2018, VL-360, IS-17, P-3220-3227, DO-https://doi.org/10.1002/adsc.201800531. "Chen"). (Year: 2018).*

(Continued)

Primary Examiner — Medhanit W Bahta
Assistant Examiner — Manahil Mirghani Ali Abdalhameed
(74) Attorney, Agent, or Firm — Heslin Rothenberg Farley & Mesiti P.C.

(57) ABSTRACT

A genus of compounds encompassed by formula (III) and their use is disclosed:

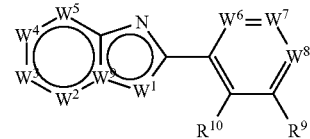

The compounds activate Ppargc1a and, as a consequence, are useful for treating a variety of neurodegenerative diseases such as amyotrophic lateral sclerosis (ALS), Alzheimer's disease, Parkinson's disease, Huntington's disease, frontotemporal degeneration, dementia with Lewy bodies, motor neuron diseases, and a demyelinating disease.

12 Claims, 3 Drawing Sheets

(56) References Cited

U.S. PATENT DOCUMENTS

| | | | |
|---|---|---|---|
| 9,233,983 B2 | 1/2016 | Thakkar et al. | |
| 10,272,070 B2 | 4/2019 | Nguyen et al. | |
| 10,583,125 B2 | 3/2020 | Nguyen et al. | |
| 10,851,066 B2 * | 12/2020 | Banister | C07D 277/66 |
| 2005/0282780 A1 | 12/2005 | Labaudiniere | |
| 2005/0282820 A1 | 12/2005 | Gontcharov et al. | |
| 2007/0037865 A1 | 2/2007 | Nunes et al. | |
| 2012/0245185 A1 * | 9/2012 | Conn | A61P 25/16 544/335 |
| 2014/0114067 A1 | 4/2014 | Pae et al. | |
| 2015/0216168 A1 * | 8/2015 | Frackenpohl | A01N 43/52 504/276 |
| 2016/0074367 A1 | 3/2016 | Rogers et al. | |
| 2020/0299244 A1 | 9/2020 | Bannister et al. | |
| 2021/0061768 A1 | 3/2021 | Kitano et al. | |
| 2021/0061769 A1 | 3/2021 | Bannister et al. | |

FOREIGN PATENT DOCUMENTS

| | | | | |
|---|---|---|---|---|
| FR | 1569337 A * | 5/1969 | | C07D 235/18 |
| JP | 2000095767 A * | 4/2000 | | |
| JP | 2000143635 A * | 5/2000 | | |
| WO | 1988003921 A1 | 6/1988 | | |
| WO | 2004099190 A1 | 11/2004 | | |
| WO | 20040099190 A1 | 11/2004 | | |
| WO | 20050282780 A1 | 12/2005 | | |
| WO | 2009127815 A1 | 10/2009 | | |
| WO | WO-2010142426 A1 * | 12/2010 | | A61K 31/4184 |
| WO | WO-2014128465 A1 * | 8/2014 | | A61P 35/00 |
| WO | WO-2014179303 A1 * | 11/2014 | | A61K 31/416 |
| WO | WO-2016061190 A1 * | 4/2016 | | A61K 31/41 |
| WO | WO-2017106050 A1 * | 6/2017 | | A61K 31/404 |
| WO | 2020033359 A1 | 2/2020 | | |

OTHER PUBLICATIONS

P. Tway et al. (Photophysical properties of benzimidazole and thiabendazole and their homologs. Effect of substituents and solvent on the nature of the transition, J. Phys. Chem., 1982, VL-86, IS-26,pp. 5223-5226, doi: 10.1021/j100223a031. (Year: 1982).*
Chem. Sci, 2015, VL-6, IS-12, p. 6792-6798, DO-10.1039/C5SC02942B. (Year: 2015).*
International Search Report issued in PCT/US2019/45229 Jan. 9, 2020.
Written Opinion of the International Searching Authority issued in PCT/US2019/45229 Jan. 9, 2020.
Extended European Search Report issued in PCT/US2016065972 Jul. 4, 2019.
Weydt, et al., The gene coding for PCG-1Î+− modifies age at onset in Huntington's Disease, Molecular Neurodegeneration, Biomed Central, Ltd., LO, vol. 4, No. 1, p. 3, XP021052334, ISSN: 1750-1326, DOIL 10. 1186/1750-1326-4-3 Jan. 8, 2009.
Soyal, et al., A greatly extended PPARGC1A genomic locus encodes several new brain-specific isoforms and influences Huntington disease age of onset+. HumanMolecular Genetics, vol. 21, No. 15, pp. 3461-3473, XP055598439, gb, ISSN: 0964-6906, DOI: 10.1093/hng/dds177 May 15, 2012.
Bottcher, et al., Myeloid cell-based therapies in neurological disorders: How far have we come?, Elsevier, Biochimica et Biophysica Acta, pp. 323-328 2016.
Beers, et al., Immune dysregulation in amyotrophic lateral sclerosis: mechanisms and emerging therapies, www.thelancet.com/neurology, vol. 18, pp. 211-220 Feb. 2019.
Wenz, Review Article, Mitochondria and PGC-1 α in Aging and Age-Associated Diseases, SAGE-Hindawi Access to Research, Journal of Aging Research, vol. 2011, Article ID 810619, 12 pages, doi:10.4061/2011/810619 Oct. 15, 2010.
Cognitive Disorder, retrieved from https://en.wikepedia.org/w/index.php?title=Cognitive_disorder&oldid=844641350 2018.
Sun, et al., In vitro and in vivo metabolite identification of a novel benzimidazole compound ZLN005 by liquid chromatography/tandem mass spectrometry, Wiley Rapid Communications in Mass Spectrometry, vol. 32, pp. 480-488 Sep. 27, 2017.
International Search Report issued in PCT/US2015/055479 Jan. 6, 2016.
Benatar, M., Lost in translation: Treatment trials in the SOD1 mouse and in human ALS, Neurobiology of Disease 26:1-13 2007.
DiBernardo, et al., Translating preclinical insights into effective human trials in ALS, Biochimica at Biophysics Acta 1762:1139-1149 2006.
Ernhoefer, et al., Mouse models of Huntington disease: variations on a theme, Disease Models & Mechanisms 2:123-129 2009.
Nazem, et al., Rodent models of neuroinflammation for Alzheimer's disease, Journal of Neuroinflammation 12:74, 15 pages 2015.
Cho, et al., SIRT1 Deficiency in Microglia Contributes to Cognitive Decline in Aging and Neurodegeneration via Epigenetic Regulation of IL-1ß Jan. 14, 2015.
Zhang, et al., "Novel Small-Molecule PGC-1a Transcriptional Regulator with Beneficial Effects on Diabetic db/db Mice", Diabetes, 62:1297-1307 2013.
Tert-Butyl 2-phenyl-1H-benzimidazole-1-carboxylate, C18H18N202, PubChem available at https://pubchem.ncbi.nim.nih.gov/compound/21863819 Oct. 14, 2019.
STN Reg. No. 1513993-57-1, entered into STN on Jan. 8, 2014. (Year: 2014) Jan. 1, 2014.
International Search Report and Written Opinion issued in PCT/US2016/065972, mailed Feb. 17, 2017. Feb. 17, 2017.
Jpn. Kokai Tokyo Koho, Chem Abstracts Accession No. 2013:717665, Document No. 158:682432, Sealing Polymer Compositions for Solar Cells, Uesugi, et al., 47 pp., 2013 2013.
CAS Reg. No. 1505410-61-6, entered into STN. on Dec. 27, 2013 (Year: 2013) 2013.
CAS Reg. No. 1511417-57-4, entered into STN. on Jan. 5, 2014 (Year: 2014) 2013.
Davies, Bioorganic & Medicinal Chemistry Letters, vol. 22, 2012, p. 2620-2623. 2012.
Simplicio, et al., Prodrugs for Amines, Molecules 13, 519-547 2008.
Tway, et al. Photophysical Properties of Benzimidazole and Thiabendazole and Their Homologues. Effect of Substituents and Solvent on the Nature of the Transition, American Chemical Society, J. Phys. Chem., vol. 86, pp. 5223-5226 1982.
Evans, et al., Moderate modulation of disease in the G93A model of ALS by the compound 2-(2-hydroxyphenyl)-penzoxazole (HBX), Elsevier, Neuroscience Letters, vol. 624, pp. 1-7 2016.
Duchowicz, et al., QSAR analysis for heterocyclic antifungals, Elsevier, ScienceDirect, Bioorganic & Medicinal Chemistry, vol. 15, pp. 2680-2689 2007.
Shi, Shi, et al.; "Gx-50 reduces β-amyloid-induced TNF-α, IL-1β, NO, and PGE2 expression and inhibits NF-κB signaling in a mouse model of Alzheimer's disease"; Eur. J. Immunol. 2016; 46:665-676.

* cited by examiner

2-ARYLBENZIMIDAZOLES AS PPARGC1A ACTIVATORS FOR TREATING NEURODEGENERATIVE DISEASES

CROSS REFERENCE TO RELATED APPLICATIONS

This application is a national phase filing under 35 U.S.C. § 371 of PCT International Application PCT/US2019/045229, filed Aug. 6, 2019. PCT/US2019/045229 claimed priority from U.S. Provisional Application No. 62/714,962, filed Aug. 6, 2018. The contents of the prior applications are incorporated by reference herein in their entirety. This application is also related to U.S. application Ser. Nos. 16/888,040 and 17/068,985 through the common parent PCT/US2019/045229.

FIELD OF THE INVENTION

The invention relates to the use of 2-aryl benzimidazole, 2-arylbenzoxazole, 2-arylbenzothiazole, 2-arylimidazo[1,2-a]pyridine, and prodrug derivatives thereof as chemical activators of Ppargc1a to treat neurodegenerative diseases.

BACKGROUND

Amyotrophic Lateral Sclerosis

Amyotrophic lateral sclerosis (ALS) is a devastating neurodegenerative disease that is characterized by the loss of motor neurons, leading to progressive decline in motor function and ultimately death. The motor symptoms of ALS include muscle weakness, twitching and wasting, which leads to difficulties in speaking, swallowing and breathing. The cause of motor neuron death in ALS is unknown and 5-10% of the ALS cases are inherited.

Activation of immune cells in the central as well as peripheral nervous system has been suggested to be a critical determinant of disease progression in ALS (Phani et al, Front Pharmacol. 3:150, 2012). Specifically, microglia and macrophages have been shown to play distinct roles in the orchestration of neuroinflammation in this disease (Dibaj et al, PLoS One. 6(3):e17910, 2011; Boillee et al, Science, 312:1389-92, 2006). Of note, bone marrow transplantation (BMT) to replace host myeloid cells has been shown to extend survival in an animal model of ALS, which was thought to be mediated by replacement of CNS microglia (Beers et al, Proc Natl Acad Sci USA. 103:16021-6, 2006). However, recent studies have shown that these cells do not develop from bone marrow cells but from more primitive yolk sac progenitors (Ginhoux et al, Science, 330:841-5, 2110), suggesting that the bone marrow derived cells that mediated the therapeutic effects of BMT in the study above are more likely peripheral or brain perivascular macrophages. Nevertheless, specific signaling pathways that contribute to innate-immune-cell-mediated inflammation in ALS remain incompletely understood.

Currently, there is no cure for ALS. Certain therapies such as riluzole, bone marrow transplantation (Deda, Cytotherapy. 11:18-25, 2009), and non-invasive ventilation (Mc-Dermott et al, BMJ, 336:658-62, 2008) have shown modest effects in improving quality of life and extending survival, but none are curative or provide dramatic benefit.

Alzheimer's Disease

Alzheimer's Disease (AD) is a degenerative brain disorder characterized clinically by progressive loss of motor function, in addition to memory, cognition, reasoning, judgment and emotional stability that gradually leads to profound mental deterioration and ultimately death. Neuronal metabolic dysfunction in the form of oxidative stress has been proposed to be an underlying cause of neurodegeneration in AD (Friedland-Leuner et al Mol Biol Transl Sci, 127:183-201, 2014).

Although AD develops differently for every individual, there are many common symptoms. Early symptoms are often mistakenly thought to be age-related concerns, or manifestations of stress. In the early stages, the most common symptoms are motor decline and difficulty in remembering recent events, known as short-term memory loss (Buchman et al, Exp Rev Neurother, 11:665-76, 2011). When AD is suspected, the diagnosis is usually based on tests that evaluate behavior and thinking abilities, often followed by a brain scan if available. However, examination of brain tissue is required for a definitive diagnosis. As the disease advances, symptoms can include confusion, irritability, aggression, mood swings, trouble with language, and long-term memory loss. As the person's condition declines, he/she often withdraws from family and society. Gradually, bodily functions are lost, ultimately leading to death.

Parkinson's Disease

Parkinson's disease (PD), also known as idiopathic or primary parkinsonism, is a degenerative neurological disorder of the central nervous system. The motor symptoms of PD result from the death of dopamine-generating cells in the substantia nigra, a region of the midbrain; the cause of this cell death is unknown. Early in the course of the disease, the most obvious symptoms are movement-related; these include shaking, rigidity, slowness of movement and difficulty with fine motor skills, walking, and gait. Later, thinking and behavioral problems may arise, with dementia commonly occurring in the advanced stages of the disease, whereas depression is the most common psychiatric symptom. Other symptoms include sensory, sleep and emotional problems.

PD is characterized by progressive motor impairment and neuroinflammation induced by microglia, the resident immune cells of the central nervous system (Aguzzi et al, Science, 339:156-61, 2013). Inflammatory mediators produced by dysfunctional microglia have been shown to induce neuronal cell death, which underlies the progressive impairment in cognitive and behavioral performance in neurodegenerative diseases (Czirr et al J Clin Invest, 122: 1156-63, 2012). Nevertheless, specific signaling pathways that contribute to microglia-mediated inflammation remain elusive.

Huntington's Disease

Huntington's disease (HD) is an autosomal dominant degenerative disorder of the central nervous system, in which the gene Huntingtin is mutated. HD is an inherited disease that causes the progressive breakdown (degeneration) of nerve cells in the brain. HD has a broad impact on a person's functional abilities and usually results in movement, thinking (cognitive) and psychiatric disorders.

The symptoms of HD vary among affected subjects; however, the progression of the disease is relatively predictable (Mason S et al, J Neurol. 2015). Early in the course of the disease, the symptoms are subtle such as changes in mood. Later, cognition and motor problems may arise, with dementia commonly occurring in the advanced stages of the disease. Chorea (involuntary movement) is the most common motor symptom. Other complications include pneumonia, heart disease, and physical injuries due to falls.

There is currently no cure for HD and full time care is required for subjects with advanced disease.

Frontotemporal Degeneration

Frontotemporal degeneration (FTD) is a disease that is closely related to AD in which progressive degeneration occurs in the frontal and temporal lobes of the brain. Gliosis and inflammatory activation of microglia have been documented in humans and animal models of FTD (Cagnin et al Annals of Neurol. 2004 6: 894-897; Yi et al. J. Exp. Med. 2010. 1:117-128). Patients with FTD experience a gradual decline in behavior and language with memory usually relatively preserved. As the disease progresses, it becomes increasingly difficult for afflicted subjects to organize activities, behave appropriately, and care for oneself. There are currently no treatments to slow or stop the progression of the disease.

Dementia with Lewy Bodies

Dementia with Lewy bodies (DLB) is a type of dementia that is related to PD. The hallmark of this disease is the presence of alpha synuclein aggregates in brains of afflicted subjects. These patients experience PD-like symptoms including hunched posture, rigid muscles, a shuffling walk and trouble initiating movement as well as changes in reasoning and thinking, memory loss (but less significantly than AD). Since Lewy bodies are also present in PD, these two diseases may be linked to the same underlying abnormalities in how the brain processes the protein alpha-synuclein. Furthermore, similar to PD, microglia-related neuroinflammation is present in brains of subjects with DLB, although this pathological feature occurs more extensively (Iannaccone et al, Parkinsonism Relat. Disord. 2.013 19: 47-52).

Motor Neuron Diseases

Motor neuron diseases (MND), are neurological disorders, similar to ALS, that selectively affect motor neurons, the cells that control voluntary muscle activity including speaking, walking, swallowing, and locomotor activities. There is no effective treatment for MND. They are neurodegenerative in nature, and cause progressive disability and death. Furthermore, a specific pathway called progranulin can trigger inflammatory activation of microglia in an animal model of MND and genetic ablation of this pathway can delay disease progression (Philips et al J Neuropathol Exp Neurol. 2010 69:1191-200).

Demyelinating Diseases

Demyelinating diseases such as Guillain-Barre syndrome and multiple sclerosis (MS) are degenerative disorders in which in which the myelin sheath of neurons is compromised.

This damage impairs signal conductivity in the affected nerves, causing deficiency in sensation, movement, cognition, or other functions. There is no cure for these diseases. Its most well-known form is MS, a disease in which the cellular subsets of the immune system have been implicated. For instance, on-going demyelination is often associated with infiltration of T cells and macrophages from the circulation as well as inflammatory-activation of microglia (Kutzelnigg et al. Handb. Clin. Neurol. 2014, 122:15-58).

The compounds described herein activate Ppargc1a and are useful for the treatment of the neurodegenerative diseases described above.

SUMMARY OF THE INVENTION

A genus of 2-arylbenzimidazoles, 2-arylbenzoxazoles, 2-arylbenzothiazoles, and 2-arylimidazo[1,2-a]pyridines has now been found that activate Ppargc1a. These compounds and prodrug derivatives thereof are useful for treatment of neurodegenerative diseases such as amyotrophic lateral sclerosis (ALS), Alzheimer's disease, Parkinson's disease, Huntington's disease, frontotemporal degeneration, dementia with Lewy bodies, a motor neuron disease, and a demyelinating disease.

In a first aspect the invention relates to compounds of formula (I):

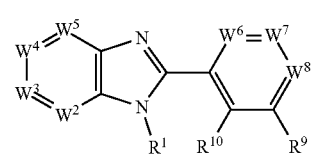

I wherein:
$W^2$ is N or C—$R^2$;
$W^3$ is N or C—$R^3$;
$W^4$ is N or C—$R^4$;
$W^5$ is N or C—$R^5$,
$W^6$ is N or C—$R^6$;
$W^7$ is N or C—$R^7$;
$W^8$ is N or C—$R^8$;

wherein:
$R^1$ is selected from —$CH_2OC(=O)R^{30}$, —$CH_2OP(=O)OR^{40}OR^{41}$, $C(=O)OR^{42}$, and $C(=O)R^{43}$;

wherein:
$R^{30}$ is chosen from ($C_1$-$C_{10}$)hydrocarbyl, ($C_1$-$C_{10}$)hydrocarbyl substituted with amino, ($C_1$-$C_{10}$)hydrocarbyl substituted with ($C_1$-$C_4$)alkoxycarbonyl, ($C_1$-$C_{10}$)hydrocarbyl substituted with carboxyl, carboxy, ($C_1$-$C_6$)alkoxycarbonyl, ($C_1$-$C_6$)alkoxycarbonylamino, methylthio, heterocyclyl, ($C_1$-$C_{10}$)oxaalkyl, $CHR^{44}NHR^{45}$, and guanidino;

wherein:
$R^{44}$ is chosen from any naturally occurring amino acid sidechain; and
$R^{45}$ is chosen from H, methyl, and ($C_1$-$C_4$)alkoxycarbonyl; and $R^{40}$ and $R^{41}$ are chosen independently from hydrogen and ($C_1$-$C_6$)hydrocarbyl;
$R^{42}$ is ($C_1$-$C_5$)alkyl; and
$R^{43}$ is ($C_1$-$C_3$)alkyl; and $R^2$, $R^3$, $R^4$ and $R^5$ are chosen independently from hydrogen, deuterium, halogen, perfluoro($C_1$-$C_4$)alkyl, ($C_1$-$C_4$)alkyl, ($C_1$-$C_4$)alkoxy, perfluoro($C_1$-$C_4$)alkoxy, ($C_1$-$C_4$)acyl, ($C_1$-$C_4$)alkoxy($C_1$-$C_4$)alkyl, hydroxy($C_1$-$C_4$)alkyl, hydroxy, carboxy, ($C_1$-$C_4$)alkoxycarbonylamino [—HNC(=O)O-alkyl], carboxamido [—C(=O)NH2], ($C_1$-$C_4$)alkylaminocarbonyl [—C(=O)NH-alkyl], cyano, acetoxy, nitro, amino, ($C_1$-$C_4$)alkylamino, di($C_1$-$C_4$)alkylamino, mercapto, ($C_1$-$C_4$)alkylthio, aminosulfonyl, ($C_1$-$C_4$)alkylsulfonyl, and ($C_1$-$C_4$)acylamino;

$R^6$ and $R^{10}$ are chosen independently from hydrogen, deuterium, halo, ($C_1$-$C_3$)alkyl, perfluoro($C_1$-$C_3$)alkyl, hydroxy, ($C_1$-$C_3$)alkoxy, perfluoro($C_1$-$C_3$)alkoxy, and amino;

$R^7$ and $R^9$ are chosen independently from hydrogen, deuterium, hydroxy, cyano, amino, halogen, halo($C_1$-$C_4$)alkyl, ($C_1$-$C_4$)alkyl, ($C_1$-$C_4$)alkoxy, and halo($C_1$-$C_4$)alkoxy; and $R^8$ is chosen from hydrogen, deuterium, halogen, halo($C_1$-$C_4$)alkyl, ($C_1$-$C_4$)alkyl, ($C_1$-$C_4$)alkoxy, halo($C_1$-$C_4$)alkoxy, cyano, phenyl, phenoxy, benzyloxy, and amino;

In a second aspect, the invention relates to compounds of formula (II):

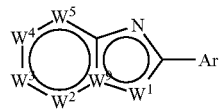

wherein:

Ar is, 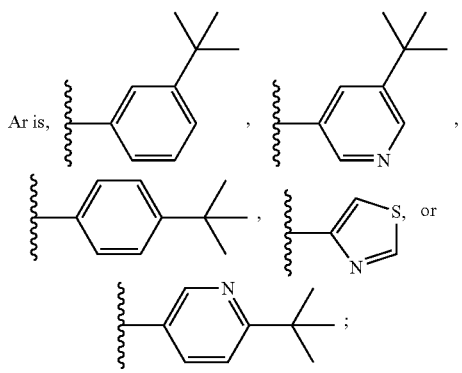

W¹ is chosen from O, S, and N—R¹, or, when W⁹ is N, W¹ may additionally be C—R⁵⁰;
W² is N or C—R²;
W³ is N or C—R³;
W⁴ is N or C—R⁴;
W⁵ is N or C—R⁵;
W⁹ is C, or, when W¹ is C—R⁵⁰; W⁹ may be N;
  wherein:
    R¹ is chosen from H, (C₁-C₃)alkyl, —CH₂OC(=O)R³⁰; —CH₂OP(=O)OR⁴⁰OR⁴¹, —C(=O)OR⁴², and —C(=O)R⁴³;
    wherein:
      R³⁰ is chosen from (C₁-C₁₀)hydrocarbyl, (C₁-C₁₀)hydrocarbyl substituted with amino, (C₁-C₁₀)hydrocarbyl substituted with (C₁-C₄)alkoxycarbonyl, (C₁-C₁₀)hydrocarbyl substituted with carboxyl, carboxy, (C₁-C₆)alkoxycarbonyl, (C₁-C₆)alkoxycarbonylamino, methylthio, heterocyclyl, (C₁-C₁₀)oxaalkyl, CHR⁴⁴NHR⁴⁵, and guanidino;
        wherein:
          R⁴⁴ is chosen from any naturally occurring amino acid sidechain; and
          R⁴⁵ is chosen from H, methyl, and (C₁-C₄)alkoxycarbonyl; and
      R⁴⁰ and R⁴¹ are chosen independently from hydrogen and (C₁-C₆)hydrocarbyl;
      R⁴² is (C₁-C₅)alkyl; and
      R⁴³ is (C₁-C₃)alkyl; and
      R⁵⁰ is H or (C₁-C₃)alkyl;
  R², R³, R⁴ and R⁵ are chosen independently from hydrogen, deuterium, halogen, perfluoro(C₁-C₄)alkyl, (C₁-C₄)alkyl, (C₁-C₄)alkoxy, perfluoro(C₁-C₄)alkoxy, (C₁-C₄)acyl, (C₁-C₄)alkoxy(C₁-C₄)alkyl, hydroxy(C₁-C₄)alkyl, hydroxy, carboxy, (C₁-C₄)alkoxycarbonylamino [—HNC(=O)O-alkyl], carboxamido [—C(=O)NH2], (C₁-C₄)alkylaminocarbonyl [—C(=O)NH-alkyl], cyano, acetoxy, nitro, amino, (C₁-C₄)alkylamino, di(C₁-C₄)alkylamino, mercapto, (C₁-C₄)alkylthio, aminosulfonyl, (C₁-C₄)alkylsulfonyl, and (C₁-C₄)acylamino;
with the proviso that Ar includes

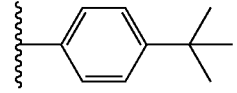 [SMILES: *c1ccc(C(C)(C)C)cc1]

only when:
W⁹ is C;
W¹ is N—R¹; and
R¹ is not H or (C₁-C₃)alkyl.

In a third aspect, the invention relates to a method of treating a neurodegenerative disease, comprising administering a compound of formula (III):

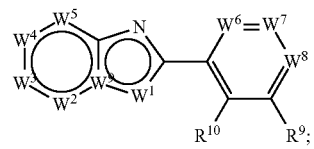

wherein:
W¹ is chosen from O, S, and N—R¹, or, when W⁹ is N, W¹ may additionally be C—R⁵⁰;
W² is N or C—R²;
W³ is N or C—R³;
W⁴ is N or C—R⁴;
W⁵ is N or C—R⁵;
W⁶ is N or C—R⁶;
W⁷ is N or C—R⁷;
W⁸ is N or C—R⁸;
W⁹ is C, or, when W¹ is C—R⁵⁰; W⁹ may be N;
  wherein:
    R¹ is chosen from H, (C₁-C₃)alkyl, —CH₂OC(=O)R³⁰, —CH₂OP(=O)OR⁴⁰OR⁴¹, —C(=O)OR⁴², and —C(=O)R⁴³;
    wherein:
      R³⁰ is chosen from (C₁-C₁₀)hydrocarbyl, (C₁-C₁₀)hydrocarbyl substituted with amino, (C₁-C₁₀)hydrocarbyl substituted with (C₁-C₄)alkoxycarbonyl, (C₁-C₁₀)hydrocarbyl substituted with carboxyl, carboxy, (C₁-C₆)alkoxycarbonyl, (C₁-C₆)alkoxycarbonylamino, methylthio, heterocyclyl, (C₁-C₁₀)oxaalkyl, CHR⁴⁴NHR⁴⁵, and guanidino;
        wherein:
          R⁴⁴ is chosen from any naturally occurring amino acid sidechain; and
          R⁴⁵ is chosen from H, methyl, and (C₁-C₄)alkoxycarbonyl; and
      R⁴⁰ and R⁴¹ are chosen independently from hydrogen and (C₁-C₆)hydrocarbyl;
      R⁴² is (C₁-C₅)alkyl; and
      R⁴³ is (C₁-C₃)alkyl; and
      R⁵⁰ is H or (C₁-C₃)alkyl;
  R², R³, R⁴ and R⁵ are chosen independently from hydrogen, deuterium, halogen, perfluoro(C₁-C₄)alkyl, (C₁-C₄)alkyl, (C₁-C₄)alkoxy, perfluoro(C₁-C₄)alkoxy, (C₁-C₄)acyl, (C₁-C₄)alkoxy(C₁-C₄)alkyl, hydroxy(C₁-C₄)alkyl, hydroxy, carboxy, (C₁-C₄)

alkoxycarbonylamino [—HNC(═O)O-alkyl], carboxamido [—C(═O)NH2], (C$_1$-C$_4$)alkylaminocarbonyl [—C(═O)NH-alkyl], cyano, acetoxy, nitro, amino, (C$_1$-C$_4$)alkylamino, di(C$_1$-C$_4$)alkylamino, mercapto, (C$_1$-C$_4$)alkylthio, aminosulfonyl, (C$_1$-C$_4$) alkylsulfonyl, and (C$_1$-C$_4$)acylamino;

R$^6$ and R$^{10}$ are chosen independently from hydrogen, deuterium, halo, (C$_1$-C$_3$)alkyl, perfluoro(C$_1$-C$_3$)alkyl, hydroxy, (C$_1$-C$_3$)alkoxy, perfluoro(C$_1$-C$_3$) alkoxy, and amino;

R$^7$ and R$^9$ are chosen independently from hydrogen, deuterium, hydroxy, cyano, amino, halogen, halo (C$_1$-C$_4$)alkyl, (C$_1$-C$_4$)alkyl, (C$_1$-C$_4$)alkoxy, and halo (C$_1$-C$_4$)alkoxy; and R$^8$ is chosen from hydrogen, deuterium, halogen, halo (C$_1$-C$_4$)alkyl, (C$_1$-C$_4$)alkyl, (C$_1$-C$_4$)alkoxy, halo(C$_1$-C$_4$)alkoxy, cyano, phenyl, phenoxy, benzyloxy, and amino;

with the proviso that R$^8$ is not hydrogen or (C$_1$-C$_4$)alkyl when:
(a) W$^1$ is N—R$^1$;
(b) R$^1$ is hydrogen;
(c) W$^2$, W$^3$, W$^4$, W$^5$, W$^6$, and W$^7$ are C—H;
(d) W$^8$ is C—R$^8$;
(e) W$^9$ is C; and
(f) R$^9$ and R$^{10}$ are hydrogen.

In a fourth aspect, the invention relates to methods and uses of the above-described compounds of formulas I, II, or III, or pharmaceutical compositions comprising a compound of formulas I, II, or III, in medicine, particularly for the treatment of a neurodegenerative disease. Such neurodegenerative diseases include amyotrophic lateral sclerosis (ALS), Alzheimer's disease, Parkinson's disease, Huntington's disease, frontotemporal degeneration, dementia with Lewy bodies, a motor neuron disease, and a demyelinating disease in a patient.

The method includes administering an effective amount of a compound or pharmaceutical composition described herein.

In a fifth aspect, the invention relates to methods and uses of the above-described compounds of formulas I, IT, or ITT, or pharmaceutical compositions comprising a compound of formulas I, II, or III, in medicine, particularly for treating aging-associated cognitive impairment and neuroinflammation in a patient. These methods include administering to a patient a therapeutically effective amount of a compound pharmaceutical composition described herein.

DETAILED DESCRIPTION OF THE INVENTION

Figure 1:
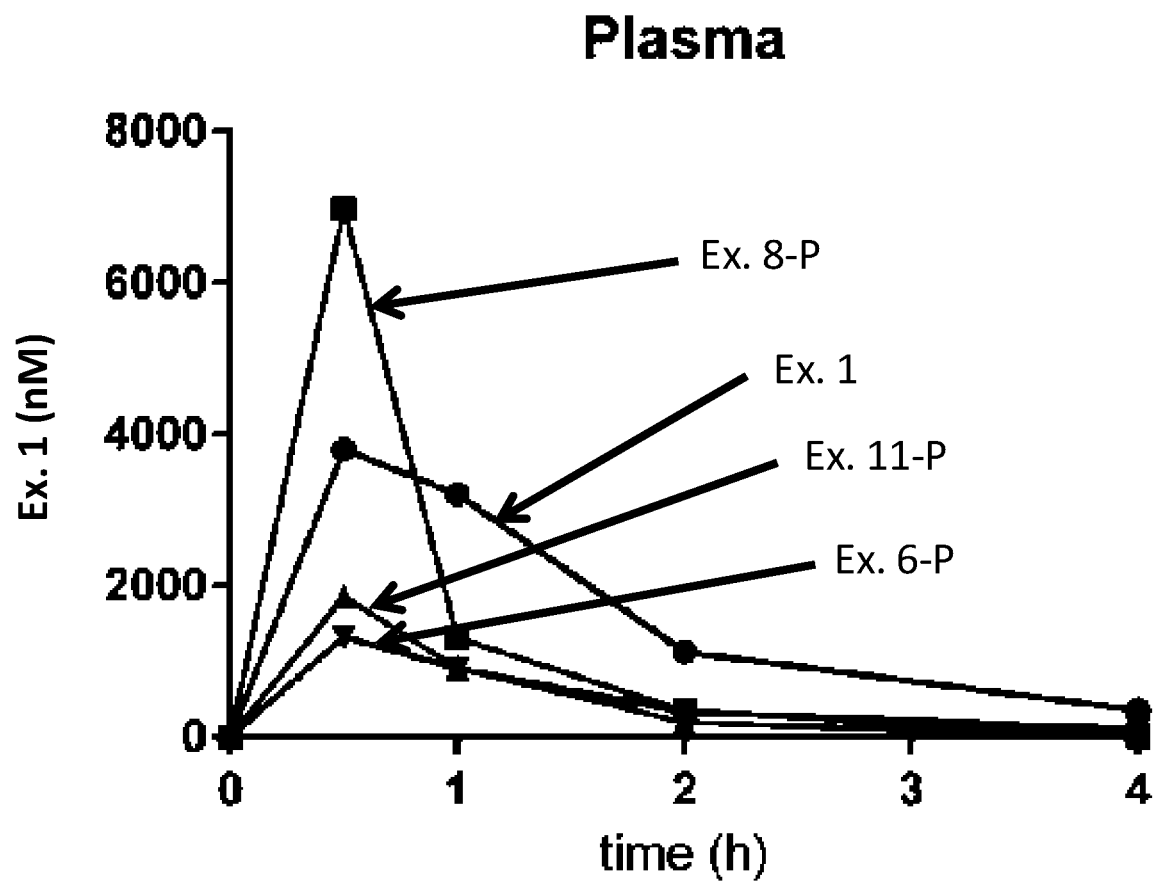
FIG. 1 shows the plasma levels of API for prodrug examples 6-P, 8-P, and 11-P.

Substituents are generally defined when introduced and retain that definition throughout the specification and in all independent claims.

In a first composition aspect, the invention relates to compounds of formula (I):

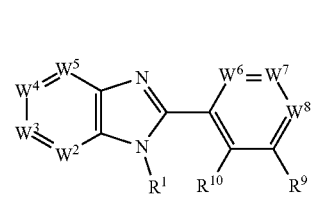

as described herein.

In a second composition aspect, the invention relates to compounds of formula (II):

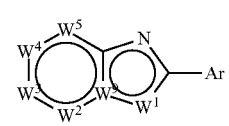

as described herein.

In a method aspect, the invention relates to compounds of formula (III):

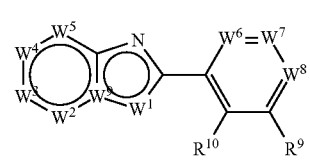

as described herein.

In the embodiments described below, the compound may be of formula I, II, or III, unless otherwise indicated.

In some embodiments of formulas II and III, W$^1$ is N—R$^1$. In other embodiments of formulas II, and III, W$^1$ is O. In yet other embodiments of formulas II and III, W$^1$ is S. In still other embodiments of formulas II and III, W$^1$ is C—R$^{50}$, preferably when W$^9$ is N. In some embodiments where W$^1$ is C—R$^{50}$, R$^{50}$ is H. In other embodiments where W$^1$ is C—R$^{50}$, R$^{50}$ is (C$_1$-C$_3$)alkyl.

In some embodiments of formulas I, II, and III, R$^1$ is —CH$_2$OC(═O)R$^{30}$; wherein R$^{30}$ is chosen from (C$_1$-C$_{10}$) hydrocarbyl, (C$_1$-C$_{10}$)hydrocarbyl substituted with amino, (C$_1$-C$_{10}$)hydrocarbyl substituted with (C$_1$-C$_4$)alkoxycarbonyl, (C$_1$-C$_{10}$)hydrocarbyl substituted with carboxyl, carboxy, (C$_1$-C$_6$)alkoxycarbonyl, (C$_1$-C$_6$)alkoxycarbonylamino, methylthio, heterocyclyl, (C$_1$-C$_{10}$)oxaalkyl, and guanidino.

In some embodiments when R$^1$ is —CH$_2$OC(═O)R$^{30}$, R$^{30}$ is chosen from: (a) (C$_1$-C$_6$)alkyl; (b) phenyl substituted with (C$_1$-C$_4$)alkylamino; (c) the descarboxy residue of a natural amino acid; (d) (C$_1$-C$_3$)hydrocarbyl substituted with carboxyl; (e) (C$_1$-C$_5$)oxaalkyl; and (d) pyridyl.

In some embodiments of formulas II and III, R$^1$ is H. In other embodiments of formulas II and III, R$^1$ is (C$_1$-C$_3$) alkyl.

In some embodiments of formulas I, II, and III, W$^2$ is N. In other embodiments of formulas I, II, and III, W$^2$ is C—R$^2$. In some embodiments, W$^2$ is chosen from C—H, C—F, C-D, C—CF$_3$, C—CH$_3$, C—Cl, C—Br, C—OH, C—OCH$_3$, C—NH$_2$, C—CF$_2$H, C—OCF$_3$, C—OCF$_2$H, C—CD$_3$, and C—CONH$_2$. In some embodiments, W$^2$ is chosen from C—H, C—F, C-D, C—CF$_2$H, C—CD$_3$, and C—CF$_3$.

In embodiments where $W^2$ is C—$R^2$, $R^2$ is chosen from hydrogen, deuterium, halogen, perfluoro($C_1$-$C_4$)alkyl, ($C_1$-$C_4$)alkyl, ($C_1$-$C_4$)alkoxy, perfluoro($C_1$-$C_4$)alkoxy, ($C_1$-$C_4$)acyl, ($C_1$-$C_4$)alkoxy($C_1$-$C_4$)alkyl, hydroxy($C_1$-$C_4$)alkyl, hydroxy, carboxy, ($C_1$-$C_4$)alkoxycarbonylamino [—HNC(=O)O-alkyl], carboxamido [—C(=O)NH2], ($C_1$-$C_4$)alkylaminocarbonyl [—C(=O)NH-alkyl], cyano, acetoxy, nitro, amino, ($C_1$-$C_4$)alkylamino, di($C_1$-$C_4$)alkylamino, mercapto, ($C_1$-$C_4$)alkylthio, aminosulfonyl, ($C_1$-$C_4$)alkylsulfonyl, and ($C_1$-$C_4$)acylamino.

In some embodiments where $W^2$ is C—$R^2$, $R^2$ is chosen from hydrogen, perfluoro($C_1$-$C_4$)alkyl, ($C_1$-$C_4$)alkyl, ($C_1$-$C_4$)alkoxy, perfluoro($C_1$-$C_4$)alkoxy, amino, hydroxy, nitrile, halo or carboxamide. In some embodiments, $R^2$ is chosen from hydrogen, trifluoromethyl, methyl, ethyl, methoxy, trifluoromethoxy, amino, hydroxy, nitrile, halo or carboxamide. In some embodiments, $R^2$ is chosen from hydrogen, halo, and perfluoro($C_1$-$C_3$)alkyl.

In some embodiments of formulas I, II, and III, $W^3$ is N. In other embodiments of formulas I, II, and III, $W^3$ is C—$R^3$. In some embodiments, $W^3$ is chosen from N, C—H, C—$NH_2$, C—F, C—$CF_3$, C-D, C—$OCH_3$, C—CN, C—OH, C—Cl, C—$CH_3$, C—$CF_2H$, C—$OCF_3$, C—$OCF_2H$, C—$CD_3$, and C—Br. In some embodiments, $W^3$ is chosen from C—H, C—$NH_2$, C—F, C—$CF_3$, C—$CF_2H$, C—$CD_3$, and C-D.

In some embodiments where $W^3$ is C—$R^3$, $R^3$ is chosen from hydrogen, deuterium, halogen, perfluoro($C_1$-$C_4$)alkyl, ($C_1$-$C_4$)alkyl, ($C_1$-$C_4$)alkoxy, perfluoro($C_1$-$C_4$)alkoxy, ($C_1$-$C_4$)acyl, ($C_1$-$C_4$)alkoxy($C_1$-$C_4$)alkyl, hydroxy($C_1$-$C_4$)alkyl, hydroxy, carboxy, ($C_1$-$C_4$)alkoxycarbonylamino [—HNC(=O)O-alkyl], carboxamido [—C(=O)NH2], ($C_1$-$C_4$)alkylaminocarbonyl [—C(=O)NH-alkyl], cyano, acetoxy, nitro, amino, ($C_1$-$C_4$)alkylamino, di($C_1$-$C_4$)alkylamino, mercapto, ($C_1$-$C_4$)alkylthio, aminosulfonyl, ($C_1$-$C_4$)alkylsulfonyl, and ($C_1$-$C_4$)acylamino.

In some embodiments where $W^3$ is C—$R^3$, $R^3$ is chosen from hydrogen, perfluoro($C_1$-$C_4$)alkyl, ($C_1$-$C_4$)alkyl, ($C_1$-$C_4$)alkoxy, perfluoro($C_1$-$C_4$)alkoxy, amino, hydroxy, nitrile, halo or carboxamide. In some embodiments where $W^3$ is C—$R^3$, $R^3$ is chosen from hydrogen, trifluoromethyl, methyl, ethyl, methoxy, trifluoromethoxy, amino, hydroxy, nitrile, halo or carboxamide. In some embodiments where $W^3$ is C—$R^3$, $R^3$ is chosen from H, halo, and perfluoro($C_1$-$C_3$)alkyl.

In some embodiments of formulas I, II, and III, $W^4$ is N. In other embodiments of formulas I, II, and III, $W^4$ is C—$R^4$. In some embodiments, $W^4$ is chosen from N, C—H, C—$NH_2$, C—F, C—$CF_3$, C-D, C—$OCH_3$, C—CN, C—OH, C—Cl, C—$CH_3$, C—$CF_2H$, C—$OCF_3$, C—$OCF_2H$, C—$CD_3$, and C—Br. In some embodiments, $W^4$ is chosen from N, C—H, C—$NH_2$, C—F, C—$CF_3$, C—$CF_2H$, C—$CD_3$, and C-D.

In some embodiments where $W^4$ is C—$R^4$, $R^4$ is chosen from hydrogen, deuterium, halogen, perfluoro($C_1$-$C_4$)alkyl, ($C_1$-$C_4$)alkyl, ($C_1$-$C_4$)alkoxy, perfluoro($C_1$-$C_4$)alkoxy, ($C_1$-$C_4$)acyl, ($C_1$-$C_4$)alkoxy($C_1$-$C_4$)alkyl, hydroxy($C_1$-$C_4$)alkyl, hydroxy, carboxy, ($C_1$-$C_4$)alkoxycarbonylamino [—HNC(=O)O-alkyl], carboxamido [—C(=O)NH2], ($C_1$-$C_4$)alkylaminocarbonyl [—C(=O)NH-alkyl], cyano, acetoxy, nitro, amino, ($C_1$-$C_4$)alkylamino, di($C_1$-$C_4$)alkylamino, mercapto, ($C_1$-$C_4$)alkylthio, aminosulfonyl, ($C_1$-$C_4$)alkylsulfonyl, and ($C_1$-$C_4$)acylamino.

In some embodiments where $W^4$ is C—$R^4$, $R^4$ is chosen from hydrogen, perfluoro($C_1$-$C_4$)alkyl, ($C_1$-$C_4$)alkyl, ($C_1$-$C_4$)alkoxy, perfluoro($C_1$-$C_4$)alkoxy, amino, hydroxy, nitrile, halo or carboxamide. In some embodiments where $W^4$ is C—$R^4$, $R^4$ is chosen from hydrogen, trifluoromethyl, methyl, ethyl, methoxy, trifluoromethoxy, amino, hydroxy, nitrile, halo or carboxamide. In some embodiments where $W^4$ is C—$R^4$, $R^4$ is chosen from H, halo, and perfluoro($C_1$-$C_3$)alkyl.

In some embodiments of formulas I, II, and III, $W^5$ is N. In other embodiments of formulas I, II, and III, $W^5$ is C—$R^5$. In some embodiments, $W^5$ is chosen from C—H, C—F, C-D, C—$CF_3$, C—$CH_3$, C—Cl, C—Br, C—OH, C—$OCH_3$, C—$NH_2$, C—$CF_2H$, C—$OCF_3$, C—$OCF_2H$, C—$CD_3$, and C—$CONH_2$. In some embodiments, $W^5$ is chosen from C—H, C—F, C-D, C—$CF_2H$, C—$CD_3$, and C—$CF_3$.

In embodiments where $W^5$ is C—$R^5$, $R^5$ is chosen from hydrogen, deuterium, halogen, perfluoro($C_1$-$C_4$)alkyl, ($C_1$-$C_4$)alkyl, ($C_1$-$C_4$)alkoxy, perfluoro($C_1$-$C_4$)alkoxy, ($C_1$-$C_4$)acyl, ($C_1$-$C_4$)alkoxy($C_1$-$C_4$)alkyl, hydroxy($C_1$-$C_4$)alkyl, hydroxy, carboxy, ($C_1$-$C_4$)alkoxycarbonylamino [—HNC(=O)O-alkyl], carboxamido [—C(=O)NH2], ($C_1$-$C_4$)alkylaminocarbonyl [—C(=O)NH-alkyl], cyano, acetoxy, nitro, amino, ($C_1$-$C_4$)alkylamino, di($C_1$-$C_4$)alkylamino, mercapto, ($C_1$-$C_4$)alkylthio, aminosulfonyl, ($C_1$-$C_4$)alkylsulfonyl, and ($C_1$-$C_4$)acylamino.

In some embodiments where $W^5$ is C—$R^5$, $R^5$ is chosen from hydrogen, perfluoro($C_1$-$C_4$)alkyl, ($C_1$-$C_4$)alkyl, ($C_1$-$C_4$)alkoxy, perfluoro($C_1$-$C_4$)alkoxy, amino, hydroxy, nitrile, halo or carboxamide. In some embodiments, $R^5$ is chosen from hydrogen, trifluoromethyl, methyl, ethyl, methoxy, trifluoromethoxy, amino, hydroxy, nitrile, halo or carboxamide. In some embodiments, $R^5$ is chosen from hydrogen, halo, and perfluoro($C_1$-$C_3$)alkyl.

In some embodiments of formulas I and III, $W^6$ is N. In other embodiments of formulas I and III, $W^6$ is C—$R^6$, preferably C—H.

In some embodiments where $W^6$ is C—$R^6$, $R^6$ is chosen from hydrogen, deuterium, halo, ($C_1$-$C_3$)alkyl, perfluoro($C_1$-$C_3$)alkyl, hydroxy, ($C_1$-$C_3$)alkoxy, perfluoro($C_1$-$C_3$)alkoxy, and amino.

In some embodiments of formulas I and ITT, $W^7$ is N. In other embodiments of formulas I and III, $W^7$ is C—$R^7$. In some embodiments where W is C—$R^7$, $R^7$ is chosen from hydrogen, deuterium, hydroxy, cyano, amino, halogen, halo($C_1$-$C_4$)alkyl, ($C_1$-$C_4$)alkyl, ($C_1$-$C_4$)alkoxy, and halo($C_1$-$C_4$)alkoxy. In some embodiments where $W^7$ is C—$R^7$, $R^7$ is hydrogen or ($C_3$-$C_4$)alkyl.

In some embodiments of formulas I and III, $W^8$ is N. In other embodiments of formulas I and III, $W^8$ is C—$R^8$. In some embodiments where $W^8$ is C—$R^8$, $R^8$ is chosen from hydrogen, deuterium, halogen, halo($C_1$-$C_4$)alkyl, ($C_1$-$C_4$)alkyl, ($C_1$-$C_4$)alkoxy, halo($C_1$-$C_4$)alkoxy, cyano, phenyl, phenoxy, benzyloxy, and amino. In some embodiments where $W^8$ is C—$R^8$, $R^8$ is chosen from H, ($C_1$-$C_4$)alkyl, amino, ($C_1$-$C_4$)alkoxy, halo($C_1$-$C_4$)alkoxy, and hydroxy. In some embodiments where $W^8$ is C—$R^8$, $R^8$ is chosen from H, tert-butyl, amino, and methoxy, preferably tert-butyl when $W^7$ is N or $R^7$ is hydrogen.

In some embodiments of formulas II and III when $W^1$ is $CR^{50}$, $W^9$ is N. In other embodiments of formulas II and III when $W^1$ is $NR^1$, O, or S, $W^9$ is C.

In some embodiments of formulas I and III, $R^9$ is chosen from hydrogen, deuterium, hydroxy, cyano, amino, halogen, halo($C_1$-$C_4$)alkyl, ($C_1$-$C_4$)alkyl, ($C_1$-$C_4$)alkoxy, and halo($C_1$-$C_4$)alkoxy. In preferred embodiments when $R^7$ is hydrogen and $R^8$ is H, $R^9$ is tert-butyl.

In some embodiments of formulas I and III, $R^{10}$ is chosen from hydrogen, deuterium, halo, ($C_1$-$C_3$)alkyl, perfluoro($C_1$-$C_3$)alkyl, hydroxy, ($C_1$-$C_3$)alkoxy, perfluoro($C_1$-$C_3$)alkoxy, and amino, preferably H.

In some embodiments of formula II, Ar is

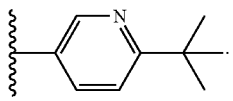

In other embodiments of formula II, Ar is

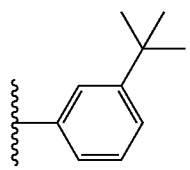 [SMILES: *c1cccc(C(C)(C)C)c1]

In still other embodiments of formula II, Ar is

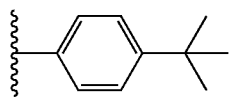

In other embodiments of formula II, Ar is

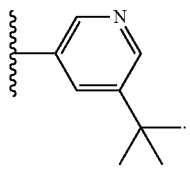

In still other embodiments of formula II, Ar is

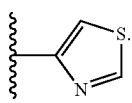

It may be found upon examination that certain species and genera are not patentable to the inventors in this application. In this case, the exclusion of species and genera in applicants' claims are to be considered artifacts of patent prosecution and not reflective of the inventors' concept or description of their invention, which encompasses all members of the genera I, II, and III that are not in the public's possession.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

While it may be possible for the compounds of formulas I, IT, and III to be administered as the raw chemical, it is preferable to present them as a pharmaceutical composition. According to a further aspect, the present invention provides a pharmaceutical composition comprising a compound of formula I or formula II, or a pharmaceutically acceptable salt thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I, II or III, or a pharmaceutically acceptable salt thereof ("active ingredient"), with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use.

Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature.

Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formulas I, II, and III of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating neurodegenerative diseases in a patient, the method comprising administering to the patient a therapeutically effective amount of a compound of formulas I, II, or III.

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

The terms "administer", "administering" or "administration" in reference to a dosage form of the invention refers to the act of introducing the dosage form into the system of subject in need of treatment. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

Throughout this specification the terms and substituents retain their definitions.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthyl ethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

The term "halogen" means fluorine, chlorine, bromine or iodine atoms. In one embodiment, halogen may be a fluorine or chlorine atom.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)$NH_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclyl alkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine.

Substituents $R''$ are generally defined when introduced and retain that definition throughout the specification and in all independent claims. For any and all compounds shown or claimed, wherein tautomerism is possible, all possible tautomers are intended to be included.

EXPERIMENTAL SECTION

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1$^{st}$ Ed., Oxford University Press, 2000; and in *March's Advanced Organic chemistry: Reactions, Mechanisms, and Structure*, 5$^{th}$ Ed., Wiley-Interscience Publication, 2001.

Benzimidazole compounds were synthesized by either: i) reaction of optionally substituted 2-nitroanilines with aryl aldehydes in the presence of sodium hydrosulfite (D. Fokas et al. *Synthesis*. 2005, 1, 47-56.); or ii) reaction of acid chlorides with optionally substituted 1,2-phenylenediamines followed by cyclocondensation of the intermediate amides.

Method A—Benzimidazoles from Reaction of 2-Nitroanilines with Aryl Aldehydes

Example 1. 2-(4-(tert-Butyl)phenyl)-1H-benzo[d]imidazole

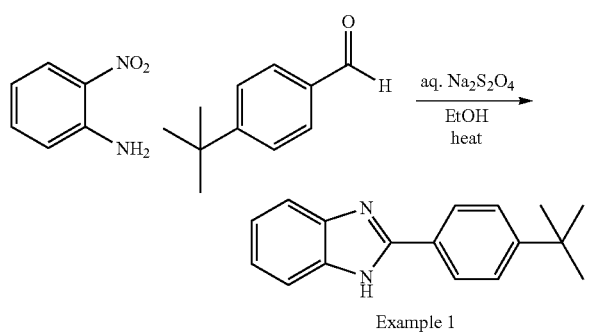

Example 1

A solution of 2-nitroaniline (691 mg, 5.00 mmol) and 4-tert-butylbenzaldehyde (836 µL, 5.00 mmol, 1.0 equiv.) in ethanol (20 mL) was treated with a freshly prepared solution of 1 M aqueous sodium hydrosulfite (15 mL, 15.0 mmol, 3.0 equiv.) and the mixture heated at 70° C. for 14 h. The mixture was cooled to ambient temperature, quenched by the addition of 5 M aqueous ammonium hydroxide (10 mL), and the formed solid collected by filtration and washed several times with water. The product was purified by recrystallization from ethanol-water to give an off-white solid (739 mg, 59%). $^1$H NMR (500 MHz, DMSO-$d_6$): δ 12.84 (1H, br s), 8.10 (2H, d, J=8.4 Hz), 7.57 (4H, app d, J=8.4 Hz, overlapping br), 7.21-7.17 (2H, m), 1.33 (9H, s); LCMS: rt 2.48-2.52 min, +ve ESI m/z 250.8 ([M+H]$^+$, 100%), −ve ESI m/z 248.7 (M−H]$^-$, 100%).

Method B—Benzimidazoles from Reaction of Acid Chlorides with 1,2-Phenylenediamines Followed by Cyclocondensation of the Intermediate Amides.

Example 2. 2-(4-(tert-Butyl)phenyl)-1H-imidazo[4,5-c]pyridine

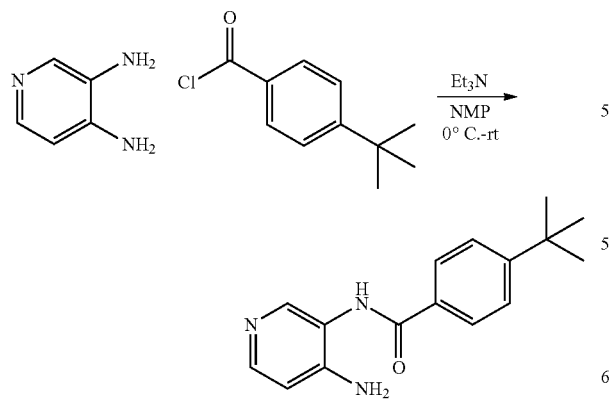

A cooled (0° C.) solution of 3,4-diaminopyridine (437 mg, 4.00 mmol) and triethylamine (669 µL, 4.80 mmol, 1.2 equiv.) in DMF (15 mL) was treated dropwise with a solution of 4-tert-butylbenzoyl chloride (781 µL. 4.00 mmol, 1.0 equiv.) in DMF (1 mL). The mixture was allowed to warm to ambient temperature, and stirred for 12 h. The mixture was slowly added to vigorously stirred ice-water (240 mL), and the formed solid collected by filtration. Purification by flash chromatography (hexane-EtOAc, 100:0 to 0:100) afforded N-(4-aminopyridin-3-yl)-4-(tert-butyl)benzamide as a white solid (369 mg, 34%). $^1$H NMR (500 MHz, DMSO-$d_6$): δ 9.66 (1H, s), 8.09 (1H, s), 7.89 (2H, d, J=8.4 Hz), 7.80 (1H, d, J=5.2 Hz), 7.55 (2H, d, J=8.4 Hz), 7.44 (1H, d, J=5.2 Hz), 5.17 (2H, s), 1.32 (9H, s); LCMS: rt 2.46-2.50 min, +ve ESI m/z 269.7 ([M+H]$^+$, 100%), −ve ESI m/z 267.7 (M−H]$^-$, 100%).

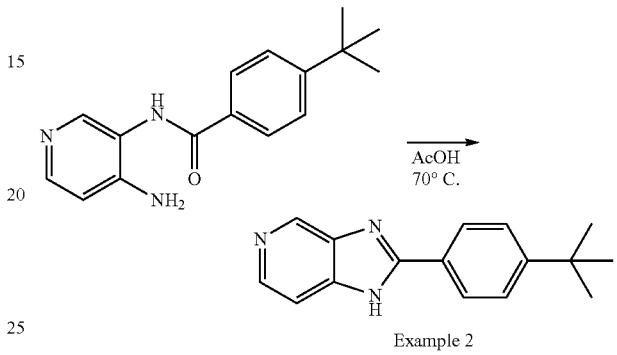

Example 2

A solution of A-(4-aminopyridin-3-yl)-4-(tert-butyl)benzamide (135 mg, 0.50 mmol) in glacial acetic acid (5 mL) was heated at 70° C. for 14 h. The solution was cooled to ambient temperature and poured into ethyl acetate (50 mL). The organic layer was washed with water (2×5 mL), saturated aqueous sodium hydrogen carbonate (2×5 mL), brine (5 mL), dried (Na$_2$SO$_4$), and the solvent evaporated under reduced pressure. The residue was resuspended in minimal ethyl acetate (~0.5 mL) and treated dropwise with hexane while stirring, and the formed precipitate was filtered and dried to give 2-(4-(tert-butyl)phenyl)-1H-imidazo[4,5-c]pyridine as a white solid (34 mg, 27%). $^1$H NMR (500 MHz, CD$_3$OD): δ 8.88 (1H, s), 8.32 (1H, d, J=5.6 Hz), 8.09 (2H, d, J=8.4 Hz), 7.64 (3H, app d, J=8.4 Hz, overlapping), 1.39 (9H, s); LCMS: rt 2.41-2.45 min, +ve ESI m/z 251.8 ([M+H]$^+$, 100%), −ve ESI m/z 249.7 (M−H]$^-$, 100%).

Benzothiazole compounds were synthesized by reacting an optionally substituted 2-aminothiophenol with an acid chloride followed by heat.

Method C—Benzothiazoles from Reaction of Acid Chlorides with 2-Aminothiophenols.

Example 3. 2-(4-tert-Butylphenyl)-1,3-benzothiazole

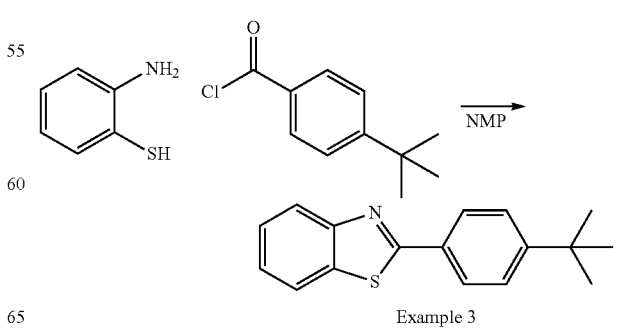

Example 3

A solution of 2-aminothiophenol (1.070 mL, 10 mmol) in NMP (20 mL) was treated dropwise with 4-tert-butylbenzoyl chloride (2.930 mL, 15 mmol, 1.5 equiv.) and the solution heated to 100° C. for 6 h. The cooled reaction was poured onto ice-water (300 mL), and the pH adjusted to 9-10 by the addition of conc. aq. NH$_4$OH. The mixture was filtered and the precipitate washed several times with water. Purification by flash chromatography (hexane-EtOAc, 100:0 to 70:30) afforded a white crystalline solid (1.831 g, 65%). $^1$H NMR (500 MHz, CDCl$_3$): δ 8.07 (1H, d, J=8.1 Hz), 8.03 (2H, d, J=8.4 Hz), 7.90 (1H, d, J=8.1 Hz), 7.52 (2H, d, J=8.4 Hz), 7.49 (1H, td, J=7.8, 0.8 Hz), 7.37 (1H, td, J=7.8, 0.8 Hz), 1.37 (9H, s); LCMS: rt 4.58-4.62 min, +ve ESI m/z 268.1 ([M+H]$^+$, 100%).

Benzoxazole compounds were synthesized by reacting an optionally substituted 2-aminophenol with an acid chloride followed by heat.

Method D—Benzoxazoles from Reaction of Acid Chlorides with 2-Aminophenols.

Example 4. 2-(4-tert-Butylphenyl)-1,3-benzoxazole

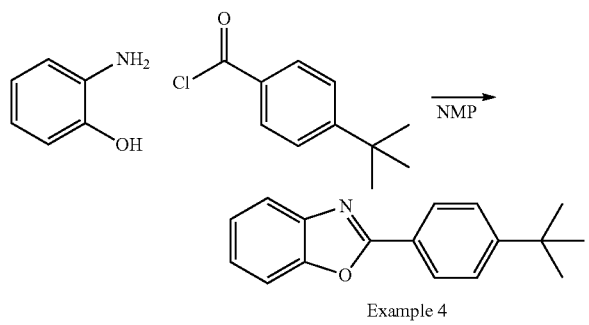

Example 4

A cooled (0° C.) solution of 2-aminophenol (1.091 mL, 10 mmol) in NMP (5 mL) was treated dropwise with tert-butyl benzoyl chloride (1.953 mL, 10 mmol, 1.0 equiv.), followed by addition of pyridine (1.011 mL, 12.5 mmol, 1.25 equiv.), and the solution stirred at 180° C. for 3 h. The reaction was poured onto water-MeOH (80:20, 20 mL), and the mixture cooled to 0° C. The precipitated product was filtered and purified by flash chromatography (hexane-EtOAc, 100:0 to 75:25) to afford a white solid (1.977 g, 75%). $^1$H NMR (500 MHz, CDCl$_3$): δ 8.19 (2H, d, J=8.5 Hz), 7.79-7.75 (1H, m), 7.59-7.57 (1H, m), 7.55 (2H, d, J=8.5 Hz), 7.36-7.33 (2H, m), 1.38 (9H, s); LCMS: rt 4.38-4.42 min, +ve ESI m/z 252.1 ([M+H]$^+$, 100%).

Imidazo[1,2-a]pyridines were synthesized by heating a 2-aminopyridine with a 2-bromo-1-phenylethan-1-one in the presence of a base.

Method E—Imidazo[1,2-a]pyridines from Reaction of a 2-Aminopyridine with a 2-Bromo-1-phenylethan-1-one.

Example 5. 2-(4-tert-Butylphenyl)imidazo[1,2-a]pyridine

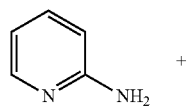 +

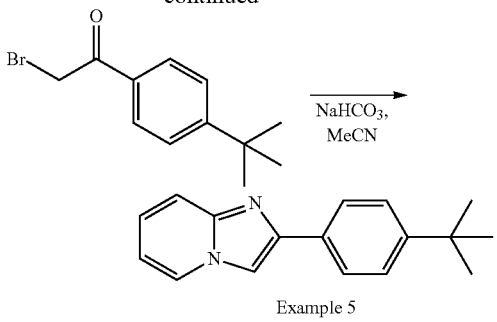

Example 5

Pyridin-2-amine (63.8 mg, 0.68 mmol) and 2-bromo-1-(4-tert-butylphenyl)ethanone (0.136 mL, 0.68 mmol) were added to a flask and dissolved in acetonitrile (2.7 mL), followed by addition of sodium bicarbonate (114 mg, 1.36 mmol). The reaction was refluxed for 1 hour and then cooled. The precipitate was removed by filtration and the filtrate evaporated with reduced pressure. The crude product was purified with flash chromatography (50:50 EtOAC:Hexane) to give 2-(4-tert-Butylphenyl)imidazo[1,2-a]pyridine (0.061 g, 35%) as a yellow solid. $^1$H NMR (500 MHz, CD$_3$OD): δ 8.42 (1H, d, J=6.9 Hz), 8.16 (1H, s), 7.85 (2H, d, J=8.4 Hz), 7.55 (1H, d, J=9.1 Hz), 7.49 (2H, d, J=8.4 Hz), 7.32 (1H, t, J=7.9 Hz), 6.92 (1H, t, J=6.8 Hz), 1.36 (9H, s); LCMS: rt 2.51-2.55 min, +ve ESI m/z 250.8 ([M+H]$^+$, 100%).

Method F—Alkylation of Benzimidazoles to Obtain 1-Alkyl-benzimidazoles.

1-Alkyl-benzimidazoles were synthesized by the dropwise addition of alkyl halides in the presence of sodium bicarbonate or sodium carbonate.

Example 6. 2-(4-tert-Butylphenyl)-1-methyl-benzo[d]imidazole

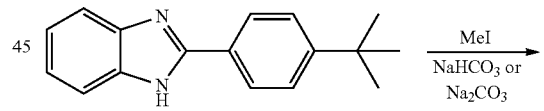

Example 6

White solid. $^1$H NMR (500 MHz, CD$_3$OD): δ 7.73 (2H, d, J=8.4 Hz), 7.68 (1H, d, J=7.9 Hz), 7.65 (2H, d, J=8.4 Hz), 7.55 (1H, d, J=7.9 Hz), 7.35 (1H, t, J=7.8 Hz), 7.31 (1H, t, J=7.8 Hz), 3.90 (3H, s), 1.40 (9H, s); LCMS: rt 2.63-2.67 min, +ve ESI m/z 264.8 ([M+H]$^-$, 100%).

The names, structures, spectroscopic data, and synthetic method (S.M.) for examples 7-78 are shown in Table 1.

TABLE 1

| Ex. # | Structure/Name | Experimental Data | S.M. |
|---|---|---|---|
| 7 | 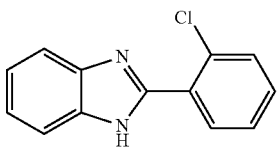 [SMILES: Clc1ccccc1-c1nc2ccccc2[nH]1]<br>2-(2-Chlorophenyl)-1H-benzo[d]imidazole | Off-white solid. $^1$H NMR (500 MHz, DMSO-d$_6$): δ 12.72 (1H, br s), 7.90 (1H, dd, J = 7.3, 1.9 Hz), 7.68-7.60 (3H, m), 7.57-7.50 (2H, m), 7.26-7.22 (2H, m); LCMS: rt 2.05-2.09 min, +ve ESI m/z 229.0 ([M + H]$^+$, 100%). | A |
| 8 | 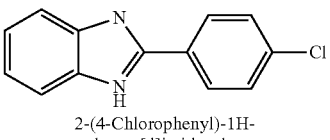<br>2-(4-Chlorophenyl)-1H-benzo[d]imidazole | Off-white solid. $^1$H NMR (500 MHz, DMSO-d$_6$): δ 12.98 (1H, br s), 8.19 (2H, d, J = 8.5 Hz), 7.67 (1H, d, J = 7.8 Hz), 7.63 (2H, d, J = 8.5 Hz), 7.54 (1H, d, J = 7.8 Hz), 7.25-7.18 (2H, m); LCMS: rt 2.25-2.29 min, +ve ESI m/z 229.1 ([M + H]$^+$, 100%), -ve ESI m/z 227.1 (M - H)$^-$, 100%). | A |
| 9 | 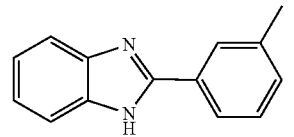 [SMILES: Cc1cccc(-c2nc3ccccc3[nH]2)c1]<br>2-(3-Methylphenyl)-1H-benzo[d]imidazole | White solid. LCMS: rt 2.11-2.15 min, +ve ESI m/z 209.1 ([M + H]$^-$, 100%), -ve ESI m/z 207.2 (M - H)$^-$, 100%). | A |
| 10 | 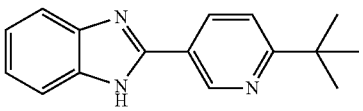 [SMILES: CC(C)(C)c1ccc(-c2nc3ccccc3[nH]2)cn1]<br>2-(6-tert-Butyl-3-pyridyl)-1H-benzo[d]imidazole | White solid $^1$H NMR (500 MHz, DMSO-d$_6$): δ 9.27 (d, 1H), 8.45-8.41 (m, 1H), 7.67-7.58 (m, 3H), 7.24-7.29 (m, 2H), 1.34 (s, 9H). | B |
| 11 | 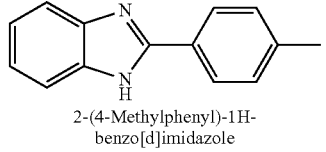<br>2-(4-Methylphenyl)-1H-benzo[d]imidazole | CAS# 120-03-6 | A |
| 12 | 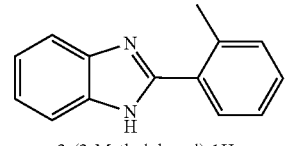<br>2-(2-Methylphenyl)-1H-benzo[d]imidazole | CAS# 2963-64-6 | A |
| 13 | 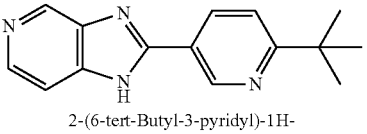<br>2-(6-tert-Butyl-3-pyridyl)-1H-imidazo[4,5-c]-pyridine | $^1$H NMR (500 MHz, Chloroform-d) δ 9.30 (s, 3H), 8.96 (s, 3H), 8.45 (d, J = 8.4 Hz, 4H), 8.28 (d, J = 5.7 Hz, 4H), 7.52-7.46 (m, 6H), 2.16 (s, 5H), 1.38 (s, 27H), 1.21 (t, J = 7.1 Hz, 1H). | B |
| 14 | 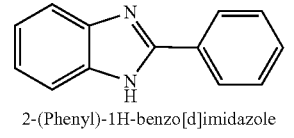<br>2-(Phenyl)-1H-benzo[d]imidazole | White solid. $^1$H NMR (500 MHz, DMSO-d$_6$): δ 12.91 (1H, br s), 8.18 (2H, d, J = 8.4 Hz), 7.62-7.48 (5H, m), 7.22-7.19 (2H, m); LCMS: rt 1.95-1.99 min, +ve ESI m/z 195.2 ([M + H]$^-$, 100%), -ve ESI m/z 193.2 (M - H)$^-$, 100%). | A |
| 15 | 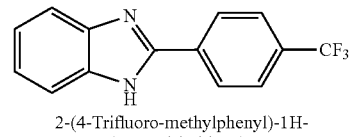<br>2-(4-Trifluoro-methylphenyl)-1H-benzo[d]imidazole | White solid. $^1$H NMR (500 MHz, DMSO-d$_6$): δ 13.17 (1H, br s), 8.39 (2H, d, J = 8.2 Hz), 7.94 (2H, d, J = 8.2 Hz), 7.71 (1H, d, J = 7.6 Hz), 7.57 (1H, d, J = 7.6 Hz), 7.28-7.21 (2H, m); LCMS: rt 2.60-2.64 min, +ve ESI m/z 263.1 ([M + H]$^+$, 100%), -ve ESI m/z 261.1 (M - H)$^-$, 100%). | A |

TABLE 1-continued

| Ex. # | Structure/Name | Experimental Data | S.M. |
|---|---|---|---|
| 16 | 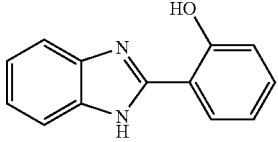 [SMILES: Oc1ccccc1-c1nc2ccccc2[nH]1]<br>2-(2-Hydroxy-phenyl)-1H-benzo[d]imidazole | Pale yellow solid. LCMS: rt 2.06-2.11 min, +ve ESI m/z 211.1 ([M + H]⁺, 100%), −ve ESI m/z 209.2 (M − H)⁻, 100%). | A |
| 17 | 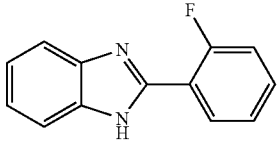<br>2-(2-Fluorophenyl)-1H-benzo[d]imidazole | White solid. $^1$H NMR (500 MHz, DMSO-$d_6$): δ 12.59 (1H, br s), 8.23 (1H, td, J = 7.7, 1.2 Hz), 7.64 (s), 7.59-7.55 (1H, m), 7.46-7.38 (2H, m), 7.25-7.21 (2H, m); LCMS: rt 1.97-2.01 min, +ve ESI m/z 213.1 ([M + H]⁺, 100%). | A |
| 18 | 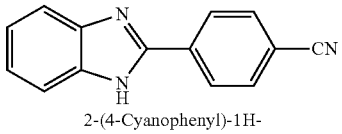<br>2-(4-Cyanophenyl)-1H-benzo[d]imidazole | Pale brown solid. $^1$H NMR (500 MHz, DMSO-$d_6$): δ 8.45 (2H, d, J = 8.4 Hz), 8.17 (2H, d, J = 8.4 Hz), 7.81-7.80 (2H, m), 7.49-7.47 (2H, m); LCMS: rt 2.21-2.25 min, +ve ESI m/z 220.1 ([M + H]⁺, 100%), −ve ESI m/z 218.1 (M − H)⁻, 100%). | A |
| 19 | 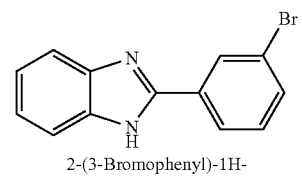<br>2-(3-Bromophenyl)-1H-benzo[d]imidazole | White solid. $^1$H NMR (500 MHz, DMSO-$d_6$): δ 13.04 (1H, br s), 8.37 (1H, s), 8.18 (1H, d, J = 7.8 Hz), 7.69 (1H, d, J = 8.0 Hz), 7.61 (2H, br), 7.52 (1H, t, J = 7.9 Hz), 7.24-7.22 (2H, m); LCMS: rt 2.38-2.42 min, +ve ESI m/z 274.9 ([M + H]⁺, 100%), −ve ESI m/z 273.0 (M − H)⁻, 100%). | A |
| 20 | 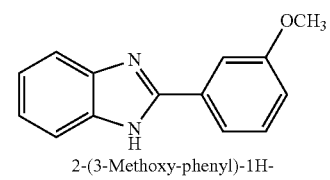<br>2-(3-Methoxy-phenyl)-1H-benzo[d]imidazole | Pale brown solid. $^1$H NMR (500 MHz, DMSO-$d_6$): δ 12.89 (1H, br s), 7.76 (1H, d, J = 7.4 Hz), 7.75 (1H, s), 7.67 (1H, d, J = 7.7 Hz), 7.53 (1H, d, J = 7.7 Hz), 7.46 (1H, t, J = 7.9 Hz), 7.24-7.17 (2H, m), 7.06 (1H, d, J = 7.4 Hz), 3.87 (3H, s); LCMS: rt 2.09-2.14 min, +ve ESI m/z 225.1 ([M + H]⁺, 100%), −ve ESI m/z 223.2 (M − H)⁻, 100%). | A |
| 21 | 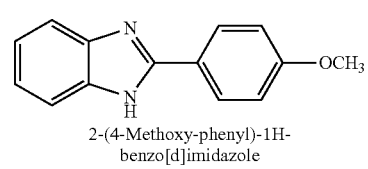<br>2-(4-Methoxy-phenyl)-1H-benzo[d]imidazole | White solid. $^1$H NMR (500 MHz, DMSO-$d_6$): δ 12.73 (1H, br s), 8.11 (2H, d, J = 8.8 Hz), 7.60 (1H, br s), 7.49 (1H, br s), 7.17 (2H, d, J = 4.5 Hz), 7.11 (2H, d, J = 8.8 Hz), 3.84 (3H, s); LCMS: rt 2.07-2.12 min, +ve ESI m/z 225.1 ([M + H]⁺, 100%), −ve ESI m/z 223.2 (M − H)⁻, 100%). | A |
| 22 | 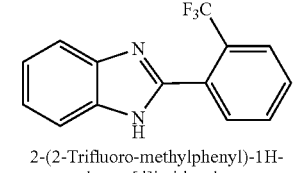<br>2-(2-Trifluoro-methylphenyl)-1H-benzo[d]imidazole | White solid. $^1$H NMR (500 MHz, DMSO-$d_6$): δ 12.76 (1H, br s), 7.95 (1H, d, J = 7.8 Hz), 7.85 (1H, t, J = 7.4 Hz), 7.81-7.76 (2H, m), 7.69 (1H, d, J = 7.8 Hz), 7.54 (1H, d, J = 7.8 Hz), 7.28-7.21 (2H, m); LCMS: rt 2.22-2.27 min, +ve ESI m/z 263.0 ([M + H]⁺, 100%), −ve ESI m/z 261.1 (M − H)⁻, 100%). | A |
| 23 | 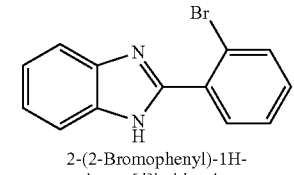<br>2-(2-Bromophenyl)-1H-benzo[d]imidazole | Pale brown solid. $^1$H NMR (500 MHz, DMSO-$d_6$): δ 12.74 (1H, br s), 7.82 (1H, d, J = 8.0 Hz), 7.76 (1H, dd, J = 7.6, 1.3 Hz), 7.62 (2H, br s), 7.56 (1H, t, J = 7.5 Hz), 7.47 (1H, td, J = 7.7, 1.2 Hz), 7.25-7.22 (2H, m); LCMS: rt 2.88-2.12 min, +ve ESI m/z 274.9 ([M + H]⁻, 100%). | A |

TABLE 1-continued

| Ex. # | Structure/Name | Experimental Data | S.M. |
|---|---|---|---|
| 24 | 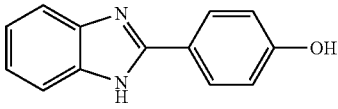<br>2-(4-Hydroxy-phenyl)-1H-benzo[d]imidazole | White solid. $^1$H NMR (500 MHz, DMSO-d$_6$): δ 12.65 (1H, br s), 9.56 (1H, br s), 8.00 (2H, d, J = 8.6 Hz), 7.54-7.52 (2H, m), 7.17-7.13 (2H, m), 6.91 (2H, d, J = 8.6 Hz); LCMS: rt 1.91-1.95 min, +ve ESI m/z 211.1 ([M + H]$^+$, 100%), −ve ESI m/z 209.2 (M − H]$^−$, 100%). | A |
| 25 | 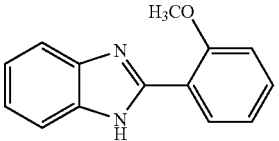<br>2-(2-Methoxy-phenyl)-1H-benzo[d]imidazole | White solid. $^1$H NMR (500 MHz, DMSO-d$_6$): δ 12.12 (1H, br s), 8.32 (1H, dd, J = 7.7, 1.4 Hz), 7.63-7.61 (2H, m), 7.48 (1H, td, J = 7.8, 1.5 Hz), 7.24 (1H, d, J = 8.3 Hz), 7.20-7.17 (2H, m), 7.12 (1H, t, J = 7.5 Hz), 4.03 (3H, s); LCMS: rt 2.11-2.15 min, +ve ESI m/z 225.1 ([M + H]$^+$, 100%). | A |
| 26 | 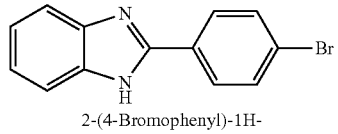<br>2-(4-Bromophenyl)-1H-benzo[d]imidazole | White solid. $^1$H NMR (500 MHz, DMSO-d$_6$): δ 13.00 (1H, br s), 8.12 (2H, d, J = 8.5 Hz), 7.77 (2H, d, J = 8.5 Hz), 7.60 (2H, br s), 7.23-7.20 (2H, m); LCMS: rt 2.28-2.32 min, +ve ESI m/z 274.9 ([M + H]$^+$, 100%), −ve ESI m/z 273.0 (M − H]$^−$, 100%). | A |
| 27 | 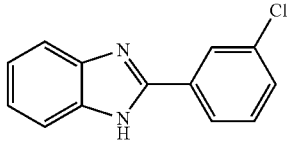 [SMILES: Brc1cccc(-c2nc3ccccc3[nH]2)c1]<br>2-(3-Chlorophenyl)-1H-benzo[d]imidazole | Pale yellow solid. $^1$H NMR (500 MHz, DMSO-d$_6$): δ 13.03 (1H, br s), 8.22 (1H, s), 8.14 (1H, d, J = 7.6 Hz), 7.65-7.55 (4H, m), 7.24-7.22 (2H, m); LCMS: rt 2.31-2.35 min, +ve ESI m/z 229.0 ([M + H]$^+$, 100%), −ve ESI m/z 227.1 (M − H]$^−$, 100%). | A |
| 28 | 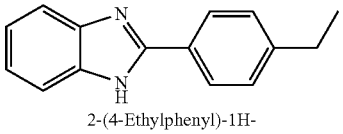<br>2-(4-Ethylphenyl)-1H-benzo[d]imidazole | White solid. $^1$H NMR (500 MHz, DMSO-d$_6$): δ 12.83 (1H, br s), 8.09 (2H, d, J = 7.9 Hz), 7.58 (2H, br s), 7.39 (2H, d, J = 7.9 Hz), 7.19 (2H, br s), 2.68 (2H, q, J = 7.6 Hz), 1.23 (3H, t, J = 7.6 Hz); LCMS: rt 2.32-2.36 min, +ve ESI m/z 223.2 ([M + H]$^+$, 100%). | A |
| 29 | 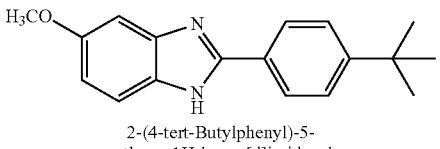<br>2-(4-tert-Butylphenyl)-5-methoxy-1H-benzo[d]imidazole | White solid. $^1$H NMR (500 MHz, DMSO-d$_6$): δ 12.67 (1H, br s), 8.05 (2H, d, J = 8.3 Hz), 7.55 (2H, d, J = 8.3 Hz), 7.46 (1H, br s), 7.06 (1H, br s), 6.82 (1H, d, J = 8.7 Hz), 3.80 (3H, s), 1.33 (9H, s); LCMS: rt 2.69-2.73 min, +ve ESI m/z 281.1 ([M + H]$^+$, 100%), −ve ESI m/z 279.2 (M − H]$^−$, 100%). | A |
| 30 | 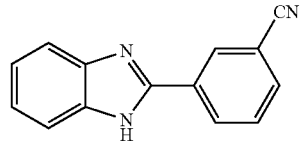 [SMILES: N#Cc1cccc(-c2nc3ccccc3[nH]2)c1]<br>2-(3-Cyanophenyl)-1H-benzo[d]imidazole | White solid. $^1$H NMR (500 MHz, DMSO-d$_6$): δ 13.10 (1H, br s), 8.56 (1H, br s), 8.49 (1H, d, J = 7.7 Hz), 7.97 (1H, d, J = 7.0 Hz), 7.78 (1H, t, J = 7.3 Hz), 7.64 (2H, br s), 7.25 (2H, br s); LCMS: rt 2.19-2.23 min, +ve ESI m/z 220.1 ([M + H]$^+$, 100%), −ve ESI m/z 218.2 (M − H]$^−$, 100%). | A |
| 31 | 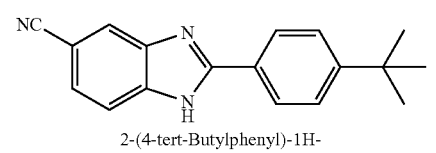<br>2-(4-tert-Butylphenyl)-1H-benzo[d]imidazole-5-carbonitrile | Pale pink solid. $^1$H NMR (500 MHz, DMSO-d$_6$): δ 13.40 (1H, br s), 8.14 (2H, d, J = 8.3 Hz), 8.11 (1H, br s), 7.74 (1H, br s), 7.62-7.58 (3H, m), 1.34 (9H, s); LCMS: rt 3.30-3.34 min, +ve ESI m/z 276.2 ([M + H]$^+$, 100%), −ve ESI m/z 274.2 (M − H]$^−$, 100%). | A |

TABLE 1-continued

| Ex. # | Structure/Name | Experimental Data | S.M. |
|---|---|---|---|
| 32 | 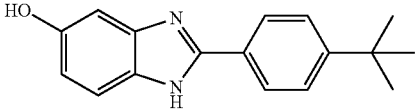<br>2-(4-tert-Butylphenyl)-1H-benzo[d]imidazol-5-ol | White solid. $^1$H NMR (500 MHz, DMSO-d$_6$): δ 12.50 (1H, br s), 9.13 (1H, br s), 8.02 (2H, d, J = 8.1 Hz), 7.53 (2H, d, J = 8.1 Hz), 7.37 (1H, br d, J = 7.3 Hz), 6.88 (1H, s), 6.67 (1H, d, J = 8.5 Hz), 1.32 (9H, s); LCMS: rt 2.52-2.57 min, +ve ESI m/z 267.1 ([M + H]$^+$, 100%), −ve ESI m/z 265.2 (M − H]$^-$, 100%). | A |
| 33 | 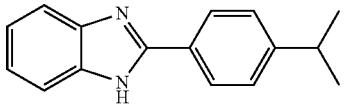 [SMILES: CC(C)c1ccc(-c2nc3ccccc3[nH]2)cc1]<br>2-(4-Isopropylphenyl)-1H-benzo[d]imidazole | White solid. $^1$H NMR (500 MHz, DMSO-d6): δ 12.84 (1H, br s), 8.09 (2H, d, J = 8.1 Hz), 7.58 (2H, br s), 7.43 (2H, d, J = 8.1 Hz), 7.19 (2H, br s), 2.97 (1H, sept., J = 6.9 Hz), 1.25 (6H, d, J = 6.9 Hz); LCMS: rt 2.46-2.50 min, +ve ESI m/z 237.2 ([M + H]$^+$, 100%), −ve ESI m/z 235.2 (M − H]$^-$, 100%). | A |
| 34 | 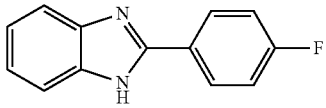 [SMILES: Fc1ccc(-c2nc3ccccc3[nH]2)cc1]<br>2-(4-Fluorophenyl)-1H-benzo[d]imidazole | Pale yellow solid. $^1$H NMR (500 MHz, DMSO-d$_6$): δ 12.92 (1H, br s), 8.22 (2H, dd, J = 8.7, 5.5 Hz), 7.59 (2H, br s), 7.41 (2H, t, J = 8.7 Hz), 7.22-7.19 (2H, m); LCMS: rt 2.02-2.06 min, +ve ESI m/z 213.1 ([M + H]$^+$, 100%), −ve ESI m/z 211.2 (M − H]$^-$, 100%). | A |
| 35 | 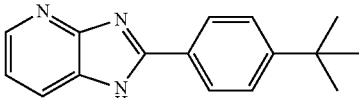<br>2-(4-tert-Butylphenyl)-1H-imidazo[4,5-b]pyridine | Off-white solid. $^1$H NMR (500 MHz, DMSO-d$_6$): δ 13.48 (1H, br s), 8.32 (1H, br s), 8.16 (2H, d, J = 8.2 Hz), 8.01 (1H, br s), 7.59 (2H, d, J = 8.2 Hz), 7.23 (1H, dd, J = 7.8, 4.8 Hz), 1.34 (9H, s); LCMS: rt 2.66-2.70 min, +ve ESI m/z 251.8 ([M + H]$^-$, 100%). | B |
| 36 | 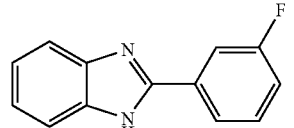<br>2-(3-Fluorophenyl)-1H-benzo[d]imidazole | Pale brown solid. $^1$H NMR (500 MHz, DMSO-d$_6$): δ 13.01 (1H, br s), 8.03 (1H, d, J = 7.8 Hz), 7.96 (1H, d, J = 10.2 Hz), 7.64-7.58 (3H, m), 7.34 (1H, t, J = 8.5 Hz), 7.25-7.21 (2H, m); LCMS: rt 2.09-2.13 min, +ve ESI m/z 213.1 ([M + H]$^+$, 100%), −ve ESI m/z 211.2 (M − H]$^-$, 100%). | A |
| 37 | 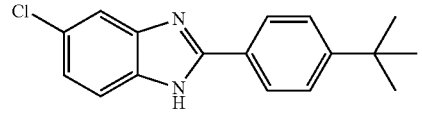<br>2-(4-tert-Butylphenyl)-5-chloro-1H-benzo[d]imidazole | White solid. $^1$H NMR (500 MHz, DMSO-d$_6$): δ 13.04 (1H, br s), 8.10 (2H, d, J = 8.3 Hz), 7.63 (2H, br s), 7.58 (2H, d, J = 8.3 Hz), 7.22 (1H, d, J = 8.5 Hz); LCMS: rt 3.10-3.15 min, +ve ESI m/z 285.1 ([M + H]$^+$, 100%), −ve ESI m/z 283.2 (M − H]$^-$, 100%). | A |
| 38 | 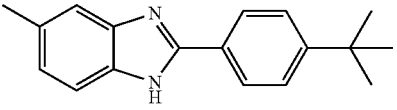<br>2-(4-tert-Butylphenyl)-5-methyl-1H-benzo[d]imidazole | White solid. $^1$H NMR (500 MHz, DMSO-d$_6$): δ 12.69 (1H, br s), 8.07 (2H, d, J = 8.4 Hz), 7.55 (2H, d, J = 8.4 Hz), 7.46 (1H, br s), 7.35 (1H, br s), 7.01 (1H, d, J = 8.0 Hz), 2.42 (3H, s), 1.33 (9H, s); LCMS: rt 2.73-2.77 min, +ve ESI m/z 265.1 ([M + H]$^+$, 100%). | A |
| 39 | 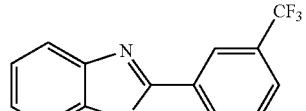<br>2-(3-Trifluoromethylphenyl)-1H-benzo[d]imidazole | Pale brown solid. $^1$H NMR (500 MHz, DMSO-d$_6$): δ 13.17 (1H, br s), 8.52 (1H, s), 8.48 (1H, d, J = 7.8 Hz), 7.86 (1H, d, J = 7.8 Hz), 7.81 (1H, t, J = 7.8 Hz), 7.64 (2H, br s), 7.26-7.23 (2H, m); LCMS: rt 2.60-2.64 min, +ve ESI m/z 263.1 ([M + H]$^+$, 100%), −ve ESI m/z 261.1 (M − H]$^-$, 100%). | A |

TABLE 1-continued

| Ex. # | Structure/Name | Experimental Data | S.M. |
|---|---|---|---|
| 40 | 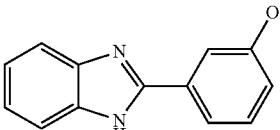<br>2-(3-Hydroxyphenyl)-1H-benzo[d]imidazole | Pale yellow solid. $^1$H NMR (500 MHz, DMSO-$d_6$): δ 12.80 (1H, br s), 9.71 (1H, s), 7.64-7.60 (4H, br m), 7.33 (1H, t, J = 7.7 Hz), 7.21-7.17 (2H, m), 6.89 (1H, dd, J = 7.7, 1.9 Hz); LCMS: rt 1.92-1.96 min, +ve ESI m/z 211.1 ([M + H]$^+$, 100%), −ve ESI m/z 209.2 (M − H)$^−$, 100%). | A |
| 41 | 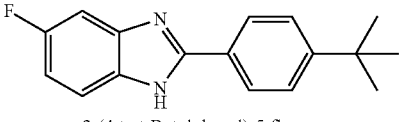<br>2-(4-tert-Butylphenyl)-5-fluoro-1H-benzo[d]imidazole | Off-white solid. $^1$H NMR (500 MHz, DMSO-$d_6$): δ 12.95 (1H, br s), 8.12-8.06 (2H, m), 7.66-7.48 (3H, m), 7.45-7.28 (1H, m), 7.09-7.01 (1H, m), 1.33 (9H, s); LCMS: rt 2.81-2.85 min, +ve ESI m/z 269.1 ([M + H]$^+$, 100%), −ve ESI m/z 267.2 (M − H)$^−$, 100%). | A |
| 42 | 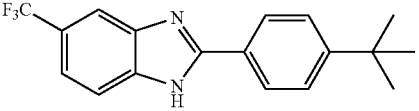 [SMILES: CC(C)(C)c1ccc(-c2nc3cc(C(F)(F)F)ccc3[nH]2)cc1]<br>(4-tert-Butylphenyl)-5-(trifluoromethyl)-1H-benzo[d]imidazole | White crystalline solid. $^1$H NMR (500 MHz, DMSO-$d_6$): δ 13.27 (1H, br s), 8.14 (2H, d, J = 8.3 Hz), 8.01 (1H, s), 8.01-7.70 (2H, m), 7.61 (2H, d, J = 8.3 Hz), 7.53-7.52 (1H, m), 1.34 (9H, s); LCMS: rt 3.53-3.57 min, +ve ESI m/z 319.1 ([M + H]$^+$, 100%), −ve ESI m/z 317.2 (M − H)$^−$, 100%). | A |
| 43 | 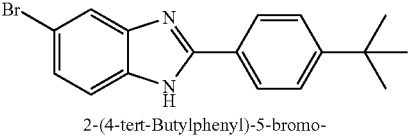<br>2-(4-tert-Butylphenyl)-5-bromo-1H-benzo[d]imidazole | Off-white solid. $^1$H NMR (500 MHz, CD$_3$OD): δ 8.01 (2H, d, J = 7.4 Hz), 7.75 (1H, br s), 7.60 (2H, d, J = 7.4 Hz), 7.51 (1H, br s), 7.37 (1H, d, J = 8.6 Hz), 1.38 (9H, s); LCMS: rt 3.19-3.23 min, +ve ESI m/z 330.6 ([M + H]$^+$, 100%), −ve ESI m/z 328.6 (M − H)$^−$, 100%). | A |
| 44 | 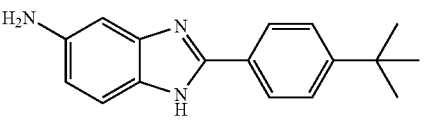 [SMILES: CC(C)(C)c1ccc(-c2nc3cc(N)ccc3[nH]2)cc1]<br>2-(4-tert-Butylphenyl)-1H-benzo[d]imidazol-5-amine | Off-white white crystalline solid. $^1$H NMR (500 MHz, DMSO-$d_6$): δ 12.23 (1H, br s), 7.98 (2H, d, J = 8.3 Hz), 7.51 (2H, d, J = 8.3 Hz), 7.26 (1H, d, J = 8.6 Hz), 6.67 (1H, s), 6.51 (1H, d, J = 8.6 Hz), 4.99 (2H, br s), 1.32 (9H, s); LCMS: rt 2.42-2.46 min, +ve ESI m/z 266.1 ([M + H]$^+$, 100%). | A |
| 45 | 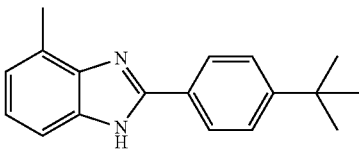 [SMILES: Cc1cccc2[nH]c(-c3ccc(C(C)(C)C)cc3)nc12]<br>2-(4-tert-Butylphenyl)-4-methyl-1H-benzo[d]imidazole | White solid. $^1$H NMR (500 MHz, DMSO-$d_6$): δ 12.78 (1H, br s), 8.13 (2H, br s), 7.57 (2H, d, J = 8.4 Hz), 7.38 (1H, br s), 7.08 (1H, t, J = 7.4 Hz), 6.98 (1H, d, J = 7.4 Hz), 2.57 (3H, s), 1.34 (9H, s); LCMS: rt 2.73-2.77 min, +ve ESI m/z 265.1 ([M + H]$^+$, 100%). | A |
| 46 | 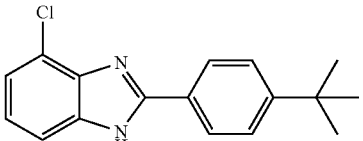<br>2-(4-tert-Butylphenyl)-4-chloro-1H-benzo[d]imidazole | Off-white solid. $^1$H NMR (500 MHz, CD$_3$OD): δ 8.08 (2H, d, J = 8.3 Hz), 7.61 (2H, d, J = 8.3 Hz), 7.48 (1H, br s), 7.26 (1H, d, J = 7.7 Hz), 7.22 (1H, t, J = 7.7 Hz), 1.39 (9H, s); LCMS: rt 3.33-3.37 min, +ve ESI m/z 285.1 ([M + H]$^+$, 100%), −ve ESI m/z 283.2 (M − H)$^−$, 100%). | A |
| 47 | 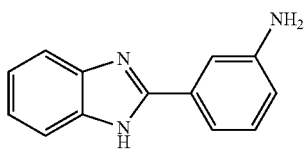 [SMILES: Nc1cccc(-c2nc3ccccc3[nH]2)c1]<br>2-(3-Aminophenyl)-1H-benzo[d]imidazole | Pale brown solid. $^1$H NMR (500 MHz, DMSO-$d_6$): δ 13.73 (1H, s), 7.61 (1H, d, J = 7.4 Hz), 7.48 (1H, d, J = 7.4 Hz), 7.42 (1H, s), 7.27 (1H, d, J = 7.6 Hz), 7.20-7.14 (3H, m), 6.67 (1H, dd, J = 7.9, 1.3 Hz), 5.31 (2H, br); LCMS: rt 1.84-1.88 min, +ve ESI m/z 210.1 ([M + H]$^+$, 100%), −ve ESI m/z 208.2 (M − H)$^−$, 100%). | A |

TABLE 1-continued

| Ex. # | Structure/Name | Experimental Data | S.M. |
|---|---|---|---|
| 48 | 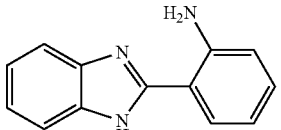<br>2-(2-Aminophenyl)-1H-benzo[d]imidazole | Pale brown solid. $^1$H NMR (500 MHz, DMSO-d$_6$): δ 12.65 (1H, br s), 7.83 (1H, d, J = 7.8 Hz), 7.64 (1H, d, J = 7.4 Hz), 7.50 (1H, d, 7.4 Hz), 7.25-7.13 (5H, m), 6.83 (1H, d, J = 8.2 Hz), 6.65 (1H, t, J = 7.5 Hz). | A |
| 49 | 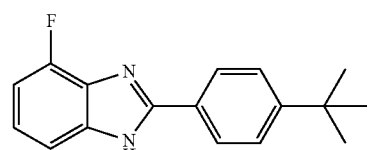<br>2-(4-tert-Butylphenyl)-4-fluoro-1H-benzo[d]imidazole | White solid. $^1$H NMR (500 MHz, CD$_3$OD): δ 8.04 (2H, d, J = 8.1 Hz), 7.59 (2H, d, J = 8.1 Hz), 7.39 (1H, br s), 7.23-7.19 (1H, m), 6.99-6.95 (1H, m), 1.38 (9H, s); LCMS: rt 3.11-3.15 min, +ve ESI m/z 268.7 ([M + H]$^+$, 100%), −ve ESI m/z 266.7 (M − H)$^−$, 100%). | A |
| 50 | 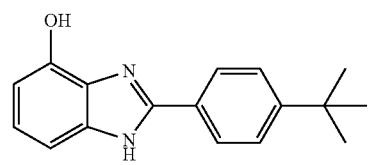<br>2-(4-tert-Butylphenyl)-1H-benzo[d]imidazol-4-ol | Pale brown solid. $^1$H NMR (500 MHz, CD$_3$OD): δ 8.02 (2H, d, J = 8.4 Hz), 7.57 (2H, d, J = 8.4 Hz), 7.10-7.03 (2H, m), 6.64-6.62 (1H, m), 1.38 (9H, s); LCMS: rt 2.50-2.54 min, +ve ESI m/z 266.7 ([M + H]$^−$, 100%), −ve ESI m/z 264.7 (M − H)$^−$, 100%). | A |
| 51 | 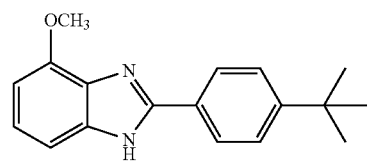<br>2-(4-tert-Butylphenyl)-4-methoxy-1H-benzo[d]imidazole | White solid. $^1$H NMR (500 MHz, CD$_3$OD): δ 8.03 (2H, d, J = 8.4 Hz), 7.57 (2H, d, J = 8.4 Hz), 7.19 (1H, br s), 7.17 (1H, t, J = 7.9 Hz), 6.77 (1H, br s), 4.01 (3H, s), 1.38 (9H, s); LCMS: rt 2.63-2.67 min, +ve ESI m/z 280.8 ([M + H]$^+$, 100%), −ve ESI m/z 278.7 (M − H)$^−$, 100%). | A |
| 52 | 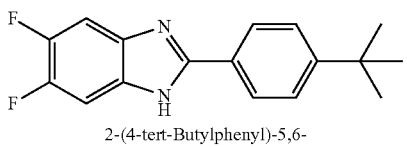<br>2-(4-tert-Butylphenyl)-5,6-difluoro-1H-benzo[d]imidazole | White solid. $^1$H NMR (500 MHz, CD$_3$OD): δ 7.98 (2H, d, J = 8.4 Hz), 7.60 (2H, d, J = 8.4 Hz), 7.45 (2H, dd, J = 9.6, 7.9 Hz), 1.38 (9H, s); LCMS: rt 3.22-3.26 min, +ve ESI m/z 286.7 ([M + H]$^−$, 100%), −ve ESI m/z 284.7 (M − H)$^−$, 100%). | A |
| 53 | 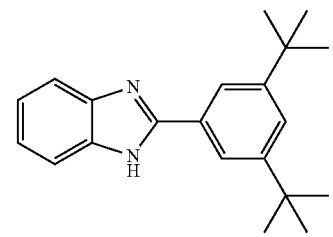<br>2-(3,5-di-tert-Butylphenyl)-1H-benzo[d]imidazole | White solid. $^1$H NMR (500 MHz, DMSO-d$_6$): δ 12.86 (1H, br s), 8.05 (2H, d, J = 1.6 Hz), 7.66 (1H, br s), 7.55 (1H, br s), 7.52 (1H, s), 7.20 (2H, br s), 1.38 (18H, s); LCMS: rt 4.21-4.25 min, +ve ESI m/z 336.9 ([M + H]$^+$, 100%), −ve ESI m/z 334.8 (M − H)$^−$, 100%). | A |
| 54 | 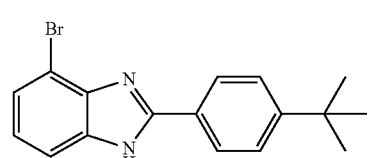<br>2-(4-tert-Butylphenyl)-4-bromo-1H-benzo[d]imidazole | Pale yellow solid. $^1$H NMR (500 MHz, CD$_3$OD): δ 8.07 (2H, d, J = 8.4 Hz), 7.60 (2H, d, J = 8.4 Hz), 7.54 (1H, br s), 7.42 (1H, d, J = 7.8 Hz), 7.15 (1H, t, J = 7.8 Hz), 1.38 (9H, s); LCMS: rt 3.40-3.44 min, +ve ESI m/z 330.6 ([M + H]$^+$, 100%), −ve ESI m/z 328.6 (M − H)$^−$, 100%). | A |

TABLE 1-continued

| Ex. # | Structure/Name | Experimental Data | S.M. |
|---|---|---|---|
| 55 | 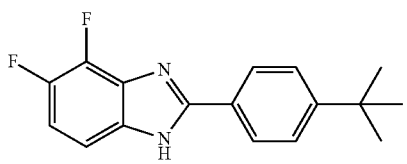<br>2-(4-tert-Butylphenyl)-4,5-difluoro-1H-benzo[d]imidazole | White solid. $^1$H NMR (500 MHz, CD$_3$OD): δ 8.03 (2H, d, J = 8.3 Hz), 7.60 (2H, d, J = 8.3 Hz), 7.32-7.30 (1H, m), 7.18-7.13 (1H, m), 1.38 (9H, s); LCMS: rt 3.52-3.56 min, +ve ESI m/z 286.7 ([M + H]$^+$, 100%), −ve ESI m/z 284.7 (M − H]$^-$, 100%). | A |
| 56 | 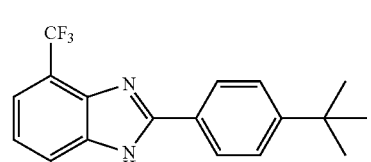<br>2-(4-tert-Butylphenyl)-4-(trifluoromethyl)-1H-benzo[d]imidazole | Off-white solid. $^1$H NMR (500 MHz, CD$_3$OD): δ 8.10 (2H, d, J = 8.3 Hz), 7.97-7.78 (1H, br), 7.61 (2H, d, J = 8.3 Hz), 7.55 (1H, d, J = 7.2 Hz), 7.38 (1H, t, J = 7.2 Hz), 1.39 (9H, s); LCMS: rt 3.73-3.77 min, +ve ESI m/z 318.7 ([M + H]$^+$, 100%), −ve ESI m/z 316.7 (M − H]$^-$, 100%). | A |
| 57 | 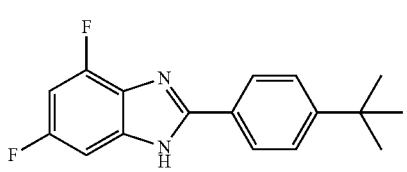 [SMILES: CC(C)(C)c1ccc(-c2nc3c(F)cc(F)cc3[nH]2)cc1]<br>2-(4-tert-Butylphenyl)-4,6-difluoro-1H-benzo[d]imidazole | Off-white crystalline solid. $^1$H NMR (500 MHz, CD$_3$OD): δ 8.02 (2H, d, J = 8.3 Hz), 7.60 (2H, d, J = 8.3 Hz), 7.12 (1H, app d, J = 8.2 Hz), 6.87 (1H, app t, J = 10.2 Hz), 1.38 (9H, s); LCMS: rt 3.54-3.58 min, +ve ESI m/z 286.7 ([M + H]$^+$, 100%), −ve ESI m/z 284.7 (M − H]$^-$, 100%). | A |
| 58 | 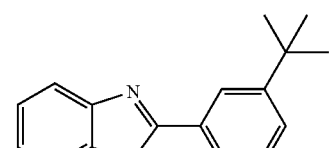<br>2-(3-tert-Butylphenyl)-1H-benzo[d]imidazole | White crystalline solid. $^1$H NMR (500 MHz, CD$_3$OD): δ 8.24 (1H, s), 7.92 (1H, d, J = 7.8 Hz), 7.63 (2H, br s), 7.60 (1H, d, J = 7.8 Hz), 7.49 (1H, d, J = 7.8 Hz), 7.30-7.26 (2H, m), 1.45 (9H, s); LCMS: rt 2.59-2.63 min, +ve ESI m/z 250.7 ([M + H]$^+$, 100%), −ve ESI m/z 248.7 (M − H]$^-$, 100%). | A |
| 59 | 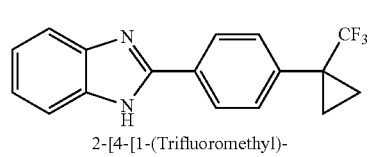<br>2-[4-[1-(Trifluoromethyl)-cyclopropyl]phenyl]-1H-benzo[d]imidazole | White solid. $^1$H NMR (500 MHz, CD$_3$OD): δ 8.10 (2H, d, J = 8.3 Hz), 7.66 (2H, d, J = 8.3 Hz), 7.62 (2H, br s), 7.29-7.26 (2H, m), 1.44-1.41 (2H, m), 1.18-1.15 (2H, m); LCMS: rt 2.64-2.68 min, +ve ESI m/z 302.7 ([M + H]$^+$, 100%), −ve ESI m/z 300.7 (M − H]$^-$, 100%). | A |
| 60 | 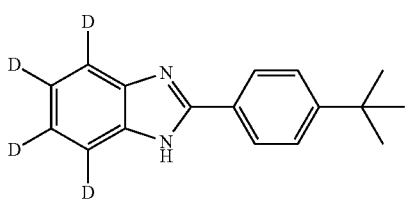 [SMILES: [2H]c1c([2H])c([2H])c2[nH]c(-c3ccc(C(C)(C)C)cc3)nc2c1[2H]]<br>2-(4-tert-Butylphenyl)-4,5,6,7-tetradeuterio-1H-benzo[d]imidazole | White solid. $^1$H NMR (500 MHz, CD$_3$OD): δ 8.02 (2H, d, J = 8.5 Hz), 7.59 (2H, d, J = 8.5 Hz), 1.38 (9H, s); LCMS: rt 2.57-2.61 min, +ve ESI m/z 254.8 ([M + H]$^+$, 100%), −ve ESI m/z 252.7 (M − H]$^-$, 100%). | A |
| 61 | 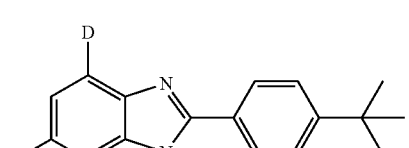<br>2-(4-tert-Butylphenyl)-4,6-dideuterio-1H-benzo[d]imidazole | White solid. $^1$H NMR (500 MHz, CD$_3$OD): δ 8.03 (2H, d, J = 8.4 Hz), 7.60 (3H, app d, J = 8.4 Hz, overlapping), 7.25 (1H, s), 1.39 (9H, s); LCMS: rt 2.57-2.61 min, +ve ESI m/z 252.8 ([M + H]$^+$, 100%), −ve ESI m/z 250.7 (M − H]$^-$, 100%). | A |

TABLE 1-continued

| Ex. # | Structure/Name | Experimental Data | S.M. |
|---|---|---|---|
| 62 | 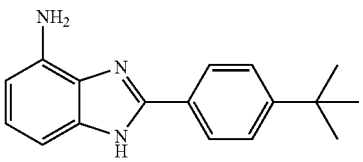 [SMILES: CC(C)(C)c1ccc(-c2nc3c(N)cccc3[nH]2)cc1]<br>2-(4-tert-Butylphenyl)-1H-benzo[d]imidazol-4-amine | Pale brown solid. $^1$H NMR (500 MHz, CD$_3$OD): δ 7.99 (2H, d, J = 8.5 Hz), 7.58 (2H, d, J = 8.5 Hz), 7.01 (1H, t, J = 7.8 Hz), 6.90 (1H, br s), 6.55 (2H, d, J = 7.6 Hz), 1.38 (9H, s); LCMS: rt 2.53-2.57 min, +ve ESI m/z 265.8 ([M + H]$^+$, 100%), −ve ESI m/z 263.6 (M − H]$^−$, 100%). | A |
| 63 | 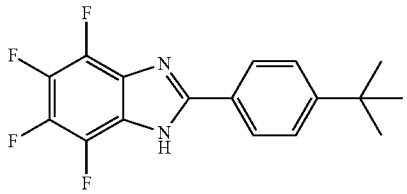 [SMILES: CC(C)(C)c1ccc(-c2nc3c(F)c(F)c(F)c(F)c3[nH]2)cc1]<br>2-(4-tert-Butylphenyl)-4,5,6,7-tetrafluoro-1H-benzo[d]imidazole | White solid. $^1$H NMR (500 MHz, CDCl$_3$): δ 9.71 (1H, br s), 7.98 (2H, d, J = 8.5 Hz), 7.98 (2H, d, J = 8.5 Hz), 1.37 (9H, s); LCMS: rt 4.01-4.05 min, +ve ESI m/z 322.8 ([M + H]$^+$, 100%), −ve ESI m/z 320.6 (M − H]$^−$, 100%). | A |
| 64 | 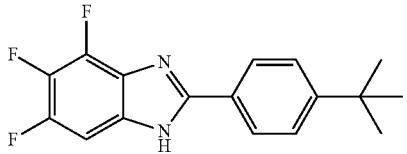 [SMILES: CC(C)(C)c1ccc(-c2nc3c(F)c(F)c(F)cc3[nH]2)cc1]<br>2-(4-tert-Butylphenyl)-4,5,6-trifluoro-1H-benzo[d]imidazole | White solid. $^1$H NMR (500 MHz, CD$_3$OD): δ 8.01 (2H, d, J = 8.5 Hz), 7.61 (2H, d, J = 8.5 Hz), 7.30-7.27 (1H, m), 1.38 (9H, s); LCMS: rt 3.73-3.77 min, +ve ESI m/z 304.8 ([M + H]$^+$, 100%), −ve ESI m/z 302.7 (M − H]$^−$, 100%). | A |
| 65 | 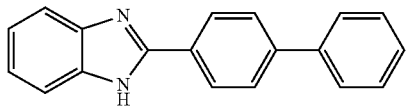 [SMILES: c1ccc(-c2ccc(-c3nc4ccccc4[nH]3)cc2)cc1]<br>2-(4-Biphenyl)-1H-benzo[d]imidazole | Pale yellow solid. $^1$H NMR (500 MHz, DMSO-d$_6$): δ 13.01 (1H, br s), 8.27 (2H, d, J = 8.3 Hz), 7.88 (2H, d, J = 8.3 Hz), 7.78 (2H, d, J = 7.5 Hz), 7.62 (2H, br s), 7.51 (2H, t, J = 7.5 Hz), 7.51 (2H, t, J = 7.5 Hz), 7.41 (1H, t, J = 7.5 Hz), 7.24-7.20 (2H, m); LCMS: rt 2.61-2.65 min, +ve ESI m/z 270.8 ([M + H]$^+$, 100%), −ve ESI m/z 268.7 (M − H]$^−$, 100%). | A |
| 66 | <br>2-(4-Trifluoromethoxyphenyl)-1H-benzo[d]imidazole | Pale yellow solid. $^1$H NMR (500 MHz, DMSO-d$_6$): δ 13.03 (1H, br s), 8.29 (2H, d, J = 8.5 Hz), 7.62 (2H, br s), 7.57 (2H, d, J = 8.5 Hz), 7.24-7.21 (2H, m); LCMS: rt 2.50-2.54 min, +ve ESI m/z 278.6 ([M + H]$^+$, 100%), −ve ESI m/z 276.6 (M − H]$^−$, 100%). | A |
| 67 | 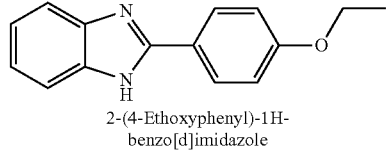<br>2-(4-Ethoxyphenyl)-1H-benzo[d]imidazole | Off-white solid. $^1$H NMR (500 MHz, DMSO-d$_6$): δ 12.76 (1H, br s), 8.09 (2H, d, J = 8.7 Hz), 7.55 (2H, br s), 7.18-7.15 (2H, m), 7.09 (2H, d, J = 8.7 Hz), 4.12 (2H, q, J = 7.0 Hz), 1.36 (3H, t, J = 7.0 Hz); LCMS: rt 2.24-2.29 min, +ve ESI m/z 238.8 ([M + H]$^+$, 100%), −ve ESI m/z 236.6 (M − H]$^−$, 100%). | A |
| 68 | 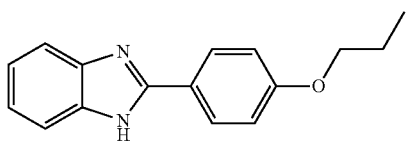 [SMILES: CCCOc1ccc(-c2nc3ccccc3[nH]2)cc1]<br>2-(4-Propoxyphenyl)-1H-benzo[d]imidazole | Off-white solid. $^1$H NMR (500 MHz, DMSO-d$_6$): δ 12.73 (1H, br s), 8.09 (2H, d, J = 8.8 Hz), 7.56 (2H, br s), 7.19-7.15 (2H, m), 7.10 (2H, d, J = 8.8 Hz), 4.02 (2H, t, J = 6.5 Hz), 1.80-1.73 (2H, m), 1.00 (3H, t, J = 7.4 Hz); LCMS: rt 2.43-2.47 min, +ve ESI m/z 252.8 ([M + H]$^+$, 100%), −ve ESI m/z 250.7 (M − H]$^−$, 100%). | A |
| 69 | 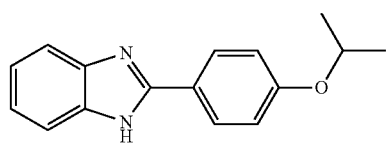<br>2-(4-Isopropoxyphenyl)-1H-benzo[d]imidazole | Off-white solid. $^1$H NMR (500 MHz, DMSO-d$_6$): δ 12.72 (1H, br s), 8.08 (2H, d, J = 8.4 Hz), 7.55 (2H, br s), 7.18-7.14 (2H, m), 7.07 (2H, d, J = 8.4 Hz), 4.72 (1H, sept, J = 6.0 Hz), 1.31 (6H, d, J = 6.0 Hz); LCMS: rt 2.37-2.41 min, +ve ESI m/z 252.8 ([M + H]$^+$, 100%), −ve ESI m/z 250.7 (M − H]$^−$, 100%). | A |

TABLE 1-continued

| Ex. # | Structure/Name | Experimental Data | S.M. |
|---|---|---|---|
| 70 | 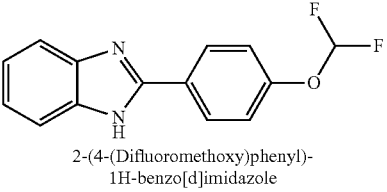<br>2-(4-(Difluoromethoxy)phenyl)-1H-benzo[d]imidazole | Pale brown solid. $^1$H NMR (500 MHz, DMSO-d$_6$): δ 12.94 (1H, br s), 8.22 (2H, d, J = 8.7 Hz), 7.59 (2H, br s), 7.363 (2H, d, J = 8.7 Hz), 7.361 (1H, t, J = 72.0 Hz), 7.22-7.19 (2H, m); LCMS: rt 2.23-2.27 min, +ve ESI m/z 260.7 ([M + H]$^+$, 100%), −ve ESI m/z 258.6 (M − H]$^−$, 100%). | A |
| 71 | 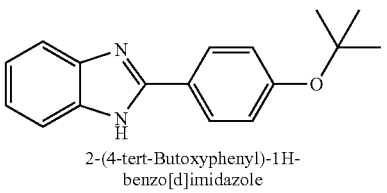<br>2-(4-tert-Butoxyphenyl)-1H-benzo[d]imidazole | Pale brown solid. $^1$H NMR (500 MHz, DMSO-d$_6$): δ 12.80 (1H, br s), 8.08 (2H, d, J = 8.7 Hz), 7.56 (2H, br s), 7.20-7.16 (2H, m), 7.14 (2H, d, J = 8.7 Hz), 1.37 (9H, s); LCMS: rt 2.44-2.48 min, +ve ESI m/z 266.8 ([M + H]$^+$, 100%), −ve ESI m/z 264.7 (M − H]$^−$, 100%). | A |
| 72 | 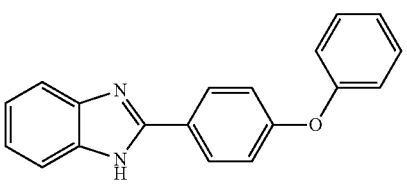 [SMILES: c1ccc(Oc2ccc(-c3nc4ccccc4[nH]3)cc2)cc1]<br>2-(4-Phenoxyphenyl)-1H-benzo[d]imidazole | Pale brown solid. $^1$H NMR (500 MHz, DMSO-d$_6$): δ 12.89 (1H, br s), 8.18 (2H, d, J = 8.5 Hz), 7.58 (2H, br s), 7.46 (2H, t, J = 7.8 Hz), 7.23-7.12 (7H, m); LCMS: rt 2.62-2.66 min, +ve ESI m/z 286.7 ([M + H]$^+$, 100%), −ve ESI m/z 284.6 (M − H]$^−$, 100%). | A |
| 73 | 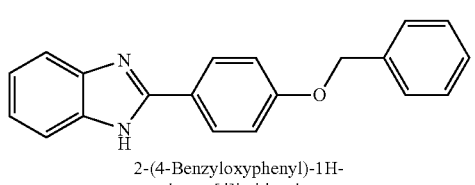<br>2-(4-Benzyloxyphenyl)-1H-benzo[d]imidazole | Off-white solid. $^1$H NMR (500 MHz, DMSO-d$_6$): δ 12.73 (1H, br s), 8.11 (2H, d, J = 8.7 Hz), 7.56 (2H, br s), 7.49 (2H, d, J = 7.4 Hz), 7.41 (2H, t, J = 7.4 Hz), 7.35 (1H, t, J = 7.4 Hz), 7.20-7.15 (4H, m), 5.20 (2H, s); LCMS: rt 2.54-2.58 min, +ve ESI m/z 300.8 ([M + H]$^+$, 100%), −ve ESI m/z 298.7 (M − H]$^−$, 100%). | A |
| 74 | 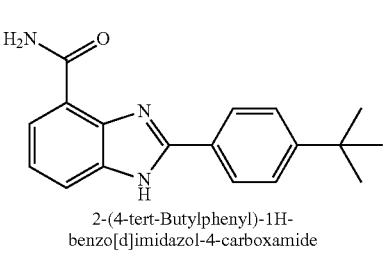<br>2-(4-tert-Butylphenyl)-1H-benzo[d]imidazol-4-carboxamide | Off-white solid. $^1$H NMR (500 MHz, DMSO-d$_6$): δ 13.32 (1H, br s), 9.37 (1H, br s), 8.16 (2H, d, J = 8.5 Hz), 7.86 (1H, d, J = 7.6 Hz), 7.76 (1H, br s), 7.72 (1H, d, J = 7.6 Hz), 7.62 (2H, d, J = 8.5 Hz), 7.34 (1H, t, J = 7.6 Hz), 1.34 (9H, s); LCMS: rt 3.07-3.11 min, +ve ESI m/z 293.9 ([M + H]$^+$, 100%), −ve ESI m/z 291.7 (M − H]$^−$, 100%). | A |
| 75 | 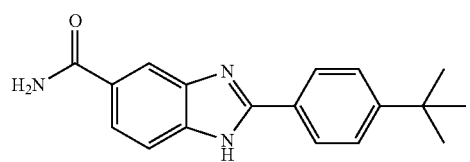 [SMILES: CC(C)(C)c1ccc(-c2nc3cc(C(N)=O)ccc3[nH]2)cc1]<br>2-(4-tert-Butylphenyl)-1H-benzo[d]imidazol-5-carboxamide | Off-white solid. $^1$H NMR (500 MHz, DMSO-d$_6$): δ 13.05 (1H, br s), 8.19 (1H, br s), 8.13 (2H, d, J = 8.5 Hz), 7.97 (1H, br s), 7.77 (1H, d, J = 8.3 Hz), 7.60 (2H, d, J = 8.5 Hz), 7.57 (1H, br s), 7.26 (1H, br s), 1.34 (9H, s); LCMS: rt 2.39-2.43 min, +ve ESI m/z 293.8 ([M + H]$^+$, 100%), −ve ESI m/z 291.7 (M − H]$^−$, 100%). | A |
| 76 | 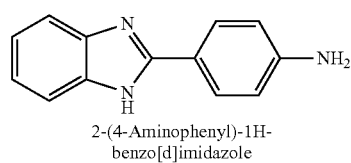<br>2-(4-Aminophenyl)-1H-benzo[d]imidazole | Pale yellow solid. $^1$H NMR (500 MHz, DMSO-d$_6$): δ 12.43 (1H, br s), 7.83 (2H, d, J = 8.5 Hz), 7.47 (2H, br s), 7.12-7.10 (2H, m), 6.66 (2H, d, J = 8.5 Hz), 5.60 (2H, br s); LCMS: rt 1.94-1.98 min, +ve ESI m/z 210.1 ([M + H]$^+$, 100%). | A |

TABLE 1-continued

| Ex. # | Structure/Name | Experimental Data | S.M. |
|---|---|---|---|
| 77 | 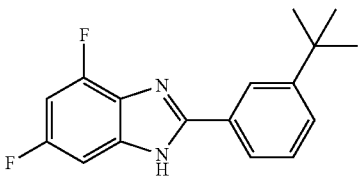 [SMILES: CC(C)(C)c1cccc(-c2nc3c(F)cc(F)cc3[nH]2)c1]<br>2-(3-tert-Butylphenyl)-4,6-difluoro-1H-benzo[d]imidazole | Off-white solid. $^1$H NMR (500 MHz, CD$_3$OD): δ 8.21 (1H, s), 7.89 (1H, d, J = 7.8 Hz), 7.60 (1H, d, J = 7.8 Hz), 7.48 (1H, t, J = 7.8 Hz), 7.14 (1H, br s), 6.89 (1H, t, J = 10.0 Hz), 1.42 (9H, s); LCMS: rt 3.65-3.69 min, +ve ESI m/z 286.7 ([M + H]$^+$, 100%), -ve ESI m/z 284.7 (M - H]$^-$, 100%). | A |
| 78 | 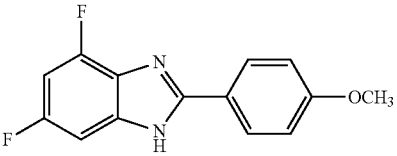 [SMILES: COc1ccc(-c2nc3c(F)cc(F)cc3[nH]2)cc1]<br>4,6-Difluoro-2-(4-methoxyphenyl)-1H-benzo[d]imidazole | Pale brown solid. $^1$H NMR (500 MHz, CD$_3$OD): δ 8.03 (2H, d, J = 8.5 Hz), 7.12 (1H, br s), 7.10 (2H, d, J = 8.5 Hz), 6.86 (1H, t, J = 10.3 Hz), 3.89 (3H, s); LCMS: rt 2.79-2.83 min, +ve ESI m/z 260.7 ([M + H]$^+$, 100%), -ve ESI m/z 258.6 (M - H]$^-$, 100%). | A |
| 79 | 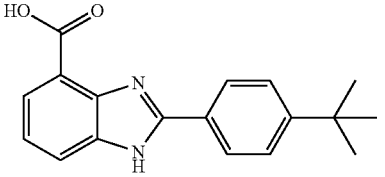 [SMILES: CC(C)(C)c1ccc(-c2nc3c(C(=O)O)cccc3[nH]2)cc1]<br>2-(4-(tert-Butyl)phenyl)-1H-benzo[d]imidazole-4-carboxylic acid | | |
| 80 | 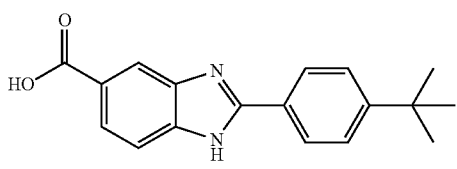 [SMILES: CC(C)(C)c1ccc(-c2nc3cc(C(=O)O)ccc3[nH]2)cc1]<br>2-(4-(tert-Butyl)phenyl)-1H-benzo[d]imidazole-5-carboxylic acid | | |
| 81 | 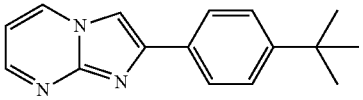 [SMILES: CC(C)(C)c1ccc(-c2cn3cccnc3n2)cc1]<br>2-(4-(tert-Butyl)phenyl)imidazo[1,2-a]pyrimidine | | |
| 82 | 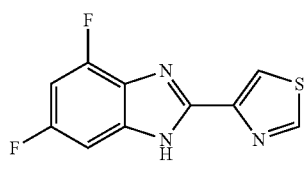 [SMILES: Fc1cc(F)c2nc(-c3cscn3)[nH]c2c1]<br>4-(4,6-Difluoro-1H-benzo[d]imidazol-2-yl)thiazole | | |

Benzimidazole prodrugs were synthesized by methods G and H as described below.

Method G—Benzimidazole Prodrugs from Reaction with Halomethylesters and Halomethyl Carbonates.

Benzimidazole prodrugs are prepared by heating benzimidazoles with chloromethyl esters in the presence of sodium iodide and sodium carbonate in refluxing acetone or, alternatively, they can be prepared by heating benzimidazoles with chloromethyl carbonates in the presence of sodium iodide and sodium carbonate in refluxing acetone (Examples 6-P to 9-P and 11-P).

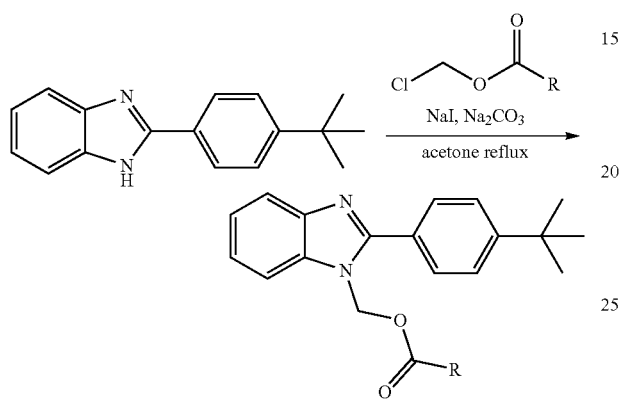

In a typical procedure as described infra, a solution of a benzimidazole (1.0 mmol) in acetone (10 mL) is treated with sodium carbonate (2.0-3.0 mmol), sodium iodide (1.0-1.5 mmol), and an optionally protected chloromethyl ester (1.0-1.5 mmol). The mixture is heated at reflux until reaction completion. The mixture is then filtered and the solvent evaporated followed by purification using flash chromatography on silica. Deprotection of the product is accomplished using standard protocols as known in the art (Examples 10-P and 12-P).

Alternatively, benzimidazoles are treated with sodium hydride, followed by the addition of bromomethyl esters to give the desired prodrugs (Example 5-P).

Example 1-P. (2-(4-(tert-Butyl)phenyl)-1H-benzo[d]imidazol-1-yl)methyl acetate

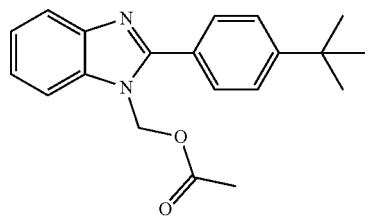 [SMILES: CC(=O)OCn1c(-c2ccc(C(C)(C)C)cc2)nc2ccccc21]

A cooled (0° C.) solution of 2-(4-tert-butylphenyl)-1H-benzimidazole (250 mg, 1.00 mmol) in DMF (5 mL) was treated portionwise with sodium hydride (60% dispersion in mineral oil, 40 mg, 1.00 mmol, 1.0 equiv.) and allowed to stir at ambient temperature for 1 h. The mixture was cooled to 0° C., treated dropwise with bromomethyl acetate (98 uL, 1.00 mmol, 1.0 equiv.), and allowed to stir at ambient temperature for 48 h. The reaction was poured into H$_2$O (100 mL) and extracted with EtOAc (4×25 mL). The combined organic layers were washed with brine (25 mL), dried (Na$_2$SO$_4$), and the solvent evaporated under reduced pressure. The crude residue was purified by flash chromatography on silica eluting with hexane-EtOAc (100:0 to 60:40) to yield the title compound as a white crystalline solid (108 mg, 32%). $^1$H NMR (500 MHz, CDCl$_3$): δ 7.83-7.81 (1H, m), 7.80 (2H, d, J=8.4 Hz), 7.62-7.60 (1H, m), 7.57 (2H, d, J=8.4 Hz), 7.36-7.33 (2H, m), 6.18 (2H, s), 2.18 (3H, s), 1.38 (9H, s). LCMS: rt 3.27-3.47 min, +ve ESI in z 322.8 ([M+H]$^+$, 100%).

Example 2-P. (2-(4-(tert-Butyl)phenyl)-1H-benzo[d]imidazol-1-yl)methyl butyrate

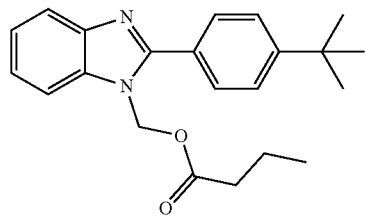 [SMILES: CCCC(=O)OCn1c(-c2ccc(C(C)(C)C)cc2)nc2ccccc21]

A mixture of 2-(4-tert-butylphenyl)-1H-benzimidazole (501 mg, 2.00 mmol), sodium carbonate (636 mg, 6.00 mmol, 3.0 equiv.), and sodium iodide (450 mg, 3.00 mmol, 1.5 equiv.) in acetone (20 mL) was treated with chloromethyl butanoate (382 µL, 3.00 mmol, 1.5 equiv.) and the mixture heated at reflux for 24 h. The mixture was cooled to ambient temperature, filtered, and the solvent evaporated under reduced pressure. The residue was purified by flash chromatography (hexane-EtOAc, 100:0 to 70:30) to give a waxy solid that was triturated with hexane to give a white solid (143 mg, 20%). $^1$H NMR (500 MHz, CDCl$_3$): δ 7.83-7.81 (1H, m), 7.80 (2H, d, J=8.4 Hz), 7.62-7.60 (1H, m), 7.56 (2H, d, J=8.4 Hz), 7.35-7.33 (2H, m), 6.18 (2H, s), 2.41 (2H, t, J=7.4 Hz), 1.74-1.67 (2H, app. sextet, J=7.4 Hz), 1.38 (9H, s), 0.96 (3H, t, J=7.4 Hz); LCMS: rt 3.62-3.78 min, +ve ESI m/z 350.9 ([M+H]$^+$, 100%).

Example 3-P. (2-(4-(tert-Butyl)phenyl)-1H-benzo[d]imidazol-1-yl)methyl isobutyrate

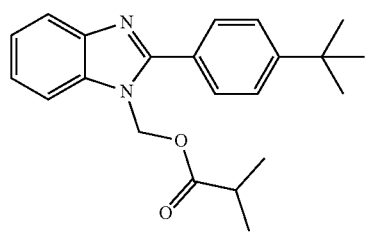 [SMILES: CC(C)C(=O)OCn1c(-c2ccc(C(C)(C)C)cc2)nc2ccccc21]

A mixture of 2-(4-tert-butylphenyl)-1H-benzimidazole (501 mg, 2.00 mmol), sodium carbonate (636 mg, 6.00 mmol, 3.0 equiv.), and sodium iodide (450 mg, 3.00 mmol, 1.5 equiv.) in acetone (20 mL) was treated with chloromethyl 2-methylpropanoate (379 µL, 3.00 mmol, 1.5 equiv.) and the mixture heated at reflux for 24 h. The mixture was cooled to ambient temperature, filtered, and the solvent evaporated under reduced pressure. The residue was purified by flash chromatography (hexane-EtOAc, 100:0 to 70:30) to give a waxy solid that was triturated with hexane to give a white solid.

Example 4-P. (2-(4-(tert-Butyl)phenyl)-1H-benzo[d]imidazol-1-yl)methyl pivalate

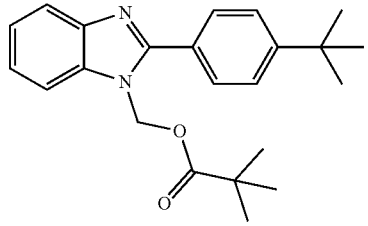 [SMILES: CC(C)(C)C(=O)OCn1c(-c2ccc(C(C)(C)C)cc2)nc2ccccc21]

A mixture of 2-(4-(tert-butylphenyl)-1H-benzimidazole (250 mg, 1.00 mmol), sodium carbonate (159 mg, 1.50 mmol, 1.5 equiv.), and sodium iodide (165 mg, 1.10 mmol, 1.1 equiv.) in acetone (10 mL) was treated with chloromethyl pivalate (159 µL, 1.10 mmol, 1.1 equiv.) and the mixture heated at reflux for 24 h. The mixture was cooled to ambient temperature, filtered, and the solvent evaporated under reduced pressure. The residue was purified by flash chromatography (hexane-EtOAc, 100:0 to 70:30) to give a white solid (41 mg, 11%). LCMS: rt 3.87-3.91 min, +ve ESI m/z 364.9 ([M+H]$^+$, 100%).

Example 5-P. tert-Butyl ((2-(4-(tert-butyl)phenyl)-1H-benzo[d]imidazol-1-yl)methyl) succinate

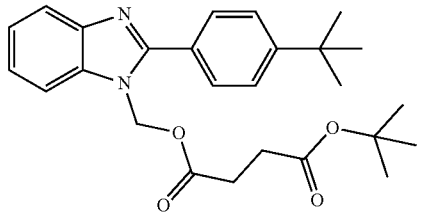 [SMILES: CC(C)(C)OC(=O)CCC(=O)OCn1c(-c2ccc(C(C)(C)C)cc2)nc2ccccc21]

A mixture of 2-(4-tert-butylphenyl)-1H-benzimidazole (1001 mg, 4.00 mmol), sodium carbonate (848 mg, 8.00 mmol, 2.0 equiv.), and sodium iodide (660 mg, 4.40 mmol, 1.1 equiv.) in acetone (40 mL) was treated with tert-butyl (chloromethyl)succinate (ClCH$_2$OC(=O)CH$_2$CH$_2$C(=O)OC(CH$_3$)$_3$) (980 mg, 4.40 mmol, 1.1 equiv.) and the mixture heated at reflux for 48 h. The mixture was cooled to ambient temperature, filtered, and the solvent evaporated under reduced pressure. The residue was purified by flash chromatography (hexane-EtOAc, 100:0 to 70:30) to give a waxy solid that was triturated with hexane to give a white solid (487 mg, 28%). NMR (500 MHz, CDCl$_3$): δ 7.83-7.80 (3H, m, overlapping), 7.61-7.59 (1H, m), 7.57 (2H, d, J=8.4 Hz), 7.35-7.33 (2H, m), 6.20 (2H, s), 2.69 (2H, t, J=6.5 Hz), 2.60 (2H, t, J=6.5 Hz), 1.41 (9H, s), 1.38 (9H, s); LCMS: rt 3.80-3.90 min, +ve ESI m/z 437.1 ([M+H]$^+$, 100%).

Example 6-P. 4-((2-(4-(tert-Butyl)phenyl)-1H-benzo[d]imidazol-1-yl)methoxy)-4-oxobutanoic acid

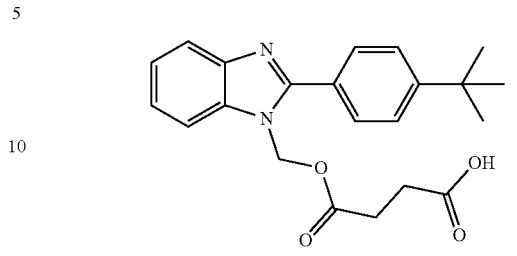

A solution of tert-butyl ((2-(4-(tert-butyl)phenyl)-1H-benzo[d]imidazol-1-yl)methyl) succinate (Example 9-P, 87 mg, 0.200 mmol) in dichloromethane (0.5 mL) was treated with trifluoroacetic acid (0.5 mL) and the solution stirred at ambient temperature for 4 h. The solution was evaporated under reduced pressure and dried under high-vacuum to afford a white crystalline solid (70 mg, 92%). $^1$H NMR (500 MHz, CDCl$_3$): δ 8.02 (1H, m), 7.92 (2H, d, J=8.1 Hz), 7.86-7.84 (1H, m), 7.71 (2H, d, J=8.1 Hz), 7.61-7.60 (2H, m), 6.32 (2H, s), 6.01 (1H, br s), 2.73 (4H, s), 1.39 (9H, s). LCMS: rt 2.90-2.94 min, +ve ESI m/z 380.9 ([M+H]$^+$, 100%).

Example 7-P. (2-(4-(tert-Butyl)phenyl)-1H-benzo[d]imidazol-1-yl)methyl 4-(((tert-butoxycarbonyl)amino)methyl)benzoate

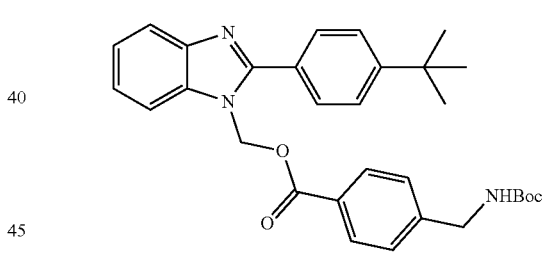

A mixture of 2-(4-tert-butylphenyl)-1H-benzimidazole (1001 mg, 4.00 mmol), sodium carbonate (1272 mg, 12.00 mmol, 3.0 equiv.), and sodium iodide (660 mg, 4.40 mmol, 1.1 equiv.) in acetone (40 mL) was treated with chloromethyl 4-(((tert-butoxycarbonyl)amino)methyl)benzoate (1319 mg, 4.40 mmol, 1.1 equiv.) and the mixture heated at reflux for 48 h. The mixture was cooled to ambient temperature, filtered, and the solvent evaporated under reduced pressure. The residue was purified by flash chromatography (hexane-EtOAc, 100:0 to 70:30) to give a white solid (532 mg, 26%). $^1$H NMR (500 MHz, CDCl$_3$): δ 8.04 (2H, d, J=8.3 Hz), 7.87-7.83 (3H, m, overlapping), 7.68-7.66 (1H, m), 7.58 (2H, d, J=8.3 Hz), 7.39-7.34 (4H, m, overlapping), 6.43 (2H, s), 4.93 (1H, br s), 4.38 (2H, d, J=5.2 Hz), 1.46 (9H, s), 1.38 (9H, s); LCMS: rt 3.88-3.92 min, +ve ESI m/z 514.1 ([M+H]$^+$, 100%).

Example 8-P. (4-(((2-(4-(tert-butyl)phenyl)-1H-benzo[d]imidazol-1-yl)methoxy)carbonyl)-phenyl)methylammonium hydrochloride

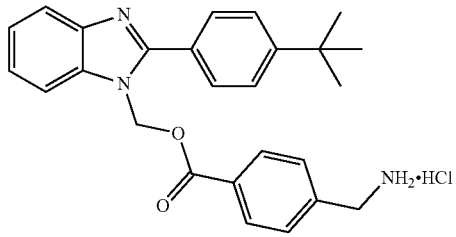

A solution of (2-(4-(tert-butyl)phenyl)-1H-benzo[d]imidazol-1-yl)methyl 4-(((tert-butoxycarbonyl)amino)methyl)benzoate (462 mg, 0.90 mmol) in ethyl acetate (13.5 mL) was treated with a solution of 2.5 M hydrogen chloride in ethanol (3.6 mL, 9.00 mmol, 10.0 equiv.) and the solution stirred at ambient temperature for 24 h. The solution was evaporated under reduced pressure and dried under vacuum. The obtained solid was recrystallized from methanol-diethyl ether to give fine white needles (337 mg, 93%). $^1$H NMR (500 MHz, CD$_3$OD): δ 8.24-8.22 (1H, m), 8.14 (2H, d, J=8.3 Hz), 8.01-7.99 (2H, m), 7.90-7.87 (3H, m), 7.76-7.70 (2H, m), 7.63-7.60 (2H, m), 6.69 (2H, s), 4.21 (2H, s), 1.45 (9H, s). LCMS: rt 2.66-2.70 min, +ve ESI m/z 414.0 ([M+H]$^+$, 20%).

Method H—Benzimidazole Prodrugs from Reaction with Dialkyl Chloromethyl-Phosphates.

Benzimidazole prodrugs are prepared by treating benzimidazoles with an excess of sodium hydride, followed by treatment with dialkyl chloromethylphosphates. In the case of di-tert-butyl chloromethylpshophates, the resultant product may be subjected to acid-mediated hydrolysis to afford the dihydrogen phosphate pro-drug. These procedures are adapted from those reported by Chassaing et al. (*J Med Chem*. 2008, 57, 1111), and Flores-Ramos et al. (*Bioorg Med Chem Lett*. 2014, 24, 5814).

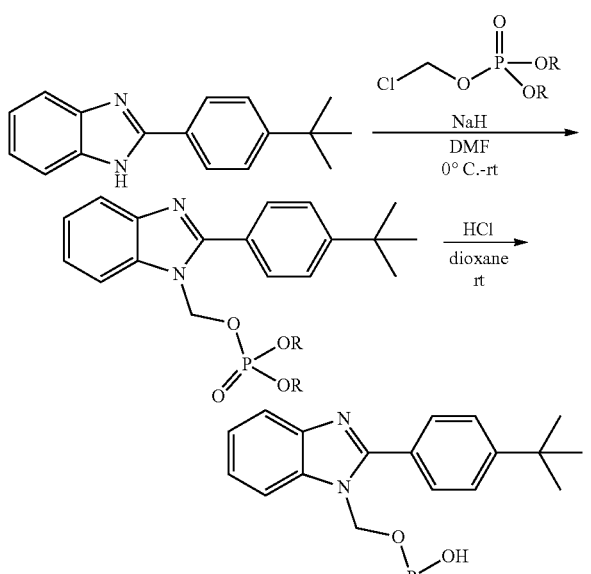

Example 9-P. Di-tert-butyl ((2-(4-(tert-butyl)phenyl)-1H-benzo[d]imidazol-1-yl)methyl) phosphate

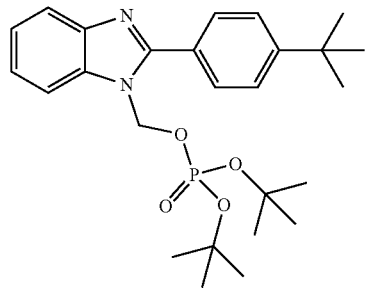 [SMILES: CC(C)(C)OP(=O)(OCn1c(-c2ccc(C(C)(C)C)cc2)nc2ccccc21)OC(C)(C)C]

To a cooled (0° C.) solution of 2-(4-(tert-butylphenyl)-1H-benzimidazole (2.00 g, 8.00 mmol) in DMF (35 mL) was added portionwise sodium hydride (60% dispersion in oil, 1.12 g, 28.0 mmol, 3.5 equiv.), and the mixture stirred at ambient temperature for 1 h. The mixture was cooled (0° C.), treated dropwise with a solution of ditert-butyl chloromethyl phosphate (2.41 mL, 10.4 mmol, 1.3 equiv.) in DMF (5 mL), and stirred at ambient temperature for 12 h. The mixture was cooled (0° C.), diluted with DCM (150 mL), and carefully treated dropwise and then portionwise with FLO (50 mL). The layers were separated and the organic layer was washed with H$_2$O (3×50 mL), brine (2×50 mL), dried (Na$_2$SO$_4$), and the solvent evaporated. The crude material was purified by flash chromatography on silica (hexane-EtOAc, 100:0 to 50:50), and the obtained oil was crystallized on storage overnight at −20° C. The crystalline mass triturated with hexanes (3×10 mL), to give a white solid (2.54 g, 64%). $^1$H NMR (500 MHz, CDCl$_3$): δ 7.87 (2H, d, J=8.4 Hz), 7.82-7.80 (1H, m), 7.76-7.74 (1H, m), 7.56 (2H, d, J=8.4 Hz), 7.36-7.32 (2H, m), 6.00 (2H, d, J=8.2 Hz), 1.43 (18H, s), 1.38 (9H, s); LCMS: rt 3.7-3.8 min, +ve ESI m/z 473.0 ([M+H]$^+$, 100%).

Example 10-P. Dihydrogen ((2-(4-(tert-butyl)phenyl)-1H-benzo[d]imidazol-1-yl)methyl) phosphate

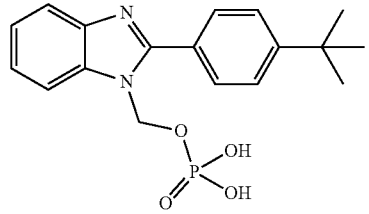 [SMILES: CC(C)(C)c1ccc(-c2nc3ccccc3n2COP(=O)(O)O)cc1]

A solution of di-tert-butyl ((2-(4-(tert-butyl)phenyl)-1H-benzo[d]imidazol-1-yl)methyl) phosphate (118 mg, 0.25 mmol) in 1,4-dioxane (0.5 mL) at ambient temperature was treated dropwise with a solution of 4 M hydrogen chloride in 1,4-dioxane (0.5 mL) and the mixture stirred for 20 h. The reaction mixture was diluted with 1,4-dioxane (1.0 mL), and the precipitate was filtered, washed with cold dioxane (1.0 mL), cold diethyl ether (1.0 mL), and dried under high-vacuum to give a white crystalline solid (69 mg, 73%). $^1$H NMR (500 MHz, DMSO-d$_6$): δ 8.04 (1H, d, J=7.9 Hz), 7.96 (2H, d, J=8.4 Hz), 7.87 (1H, d, J=7.9 Hz), 7.76 (2H, d, J=8.4 Hz), 7.62-7.56 (2H, m), 6.05 (2H, d, J=9.0 Hz), 1.37 (9H, s);

LCMS: rt 2.1-2.2 min, +ve ESI m/z 360.8 ([M+H]⁻, 100%), −ve EST m/z 358.7 ([M−H]⁻, 100%).

Example 11-P. Disodium ((2-(4-(tert-butyl)phenyl)-1H-benzo[d]imidazol-1-yl)methyl) phosphate

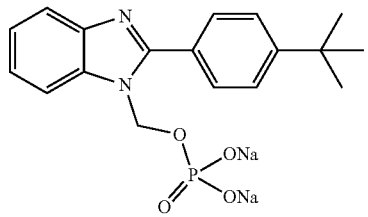

A suspension of dihydrogen ((2-(4-(tert-butyl)phenyl)-1H-benzo[d]imidazol-1-yl)methyl) phosphate (180 mg, 0.500 mmol) in methanol (5 mL) at ambient temperature was treated dropwise with a solution of 0.5 M sodium methoxide in methanol (2 mL, 1.00 mmol, 2.0 equiv.) The resultant clear solution was evaporated under reduced pressure and dried under high-vacuum to give a white solid (196 mg, 96%). $^1$H NMR (500 MHz, D$_2$O): δ 7.92-7.89 (3H, m, overlapping), 7.79-7.77 (3H, m, overlapping), 7.50 (1H, t, J=7.5 Hz), 7.46 (1H, t, J=7.5 Hz), 5.88 (2H, d, J=4.3 Hz), 1.40 (9H, s); LCMS: rt 2.06-2.10 min, +ve ESI m/z 360.8 ([M+H]⁺, 100%), −ve ESI m/z 358.7 ([M−H]⁻, 100%).

Other prodrug derivatives synthesized are as shown below. Carbamate examples were typically formed by treatment of the benzimidazole precursor with the appropriate chloroformate in pyridine/dichlormethane.

Example 12-P. (2-(4-(tert-Butyl)phenyl)-1H-benzo[d]imidazol-1-yl)methyl (tert-butoxycarbonyl)-L-alaninate

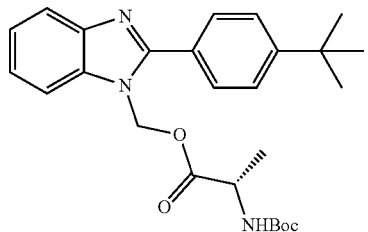 [SMILES: C[C@H](NC(=O)OC(C)(C)C)C(=O)OCn1c(-c2ccc(C(C)(C)C)cc2)nc2ccccc21]

Example 13-P. Ethyl 2-(4-(tert-butyl)phenyl)-1H-benzo[d]imidazole-1-carboxylate

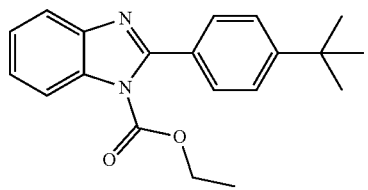 [SMILES: CCOC(=O)n1c(-c2ccc(C(C)(C)C)cc2)nc2ccccc21]

Example 14-P. Methyl 2-(4-(tert-butyl)phenyl)-1H-benzo[d]imidazole-1-carboxylate

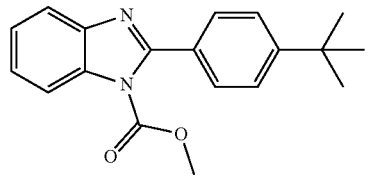 [SMILES: COC(=O)n1c(-c2ccc(C(C)(C)C)cc2)nc2ccccc21]

Example 15-P. Ethyl 2-(4-(tert-butyl)phenyl)-1H-benzo[d]imidazole-1-carboxylate

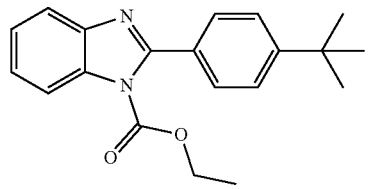 [SMILES: CCOC(=O)n1c(-c2ccc(C(C)(C)C)cc2)nc2ccccc21]

Example 16-P. Propyl 2-(4-(tert-butyl)phenyl)-1H-benzo[d]imidazole-1-carboxylate

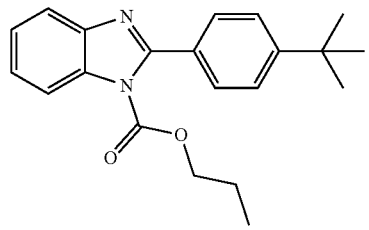 [SMILES: CCCOC(=O)n1c(-c2ccc(C(C)(C)C)cc2)nc2ccccc21]

Example 17-P. 1-(2-(4-(tert-Butyl)phenyl)-1H-benzo[d]imidazol-1-yl)ethan-1-one

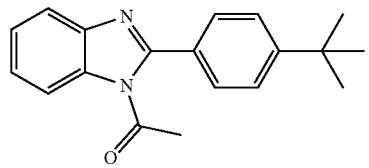 [SMILES: CC(=O)n1c(-c2ccc(C(C)(C)C)cc2)nc2ccccc21]

Biological Assays

Oxidative metabolism exerts an anti-inflammatory effect on myeloid cell phenotype (O'Neill L A, Front Immunol. 2014) and Ppargc1a can promote this energy metabolic pathway (Spiegelman B M, Novartis Found Symp. 2007). Thus, pharmacological activation of Ppargc1a would be expected to inhibit the inflammatory response of myeloid cells. This phenomenon can be measured in cultures by a TNF-α inhibition assay.

Cellular Assay Protocol to Measure TNF-α Inhibition

The murine myeloid cell line BV2 or human peripheral blood mononuclear cells (PBMC) are cultured in RPMI 1640 media (Cat #11875119, Gibco) supplemented with 10% fetal bovine serum and 1% L-glutamine 1% penicillin. These cells are then stimulated with 100 ng/ml of lipopolysaccharide (LPS, O111:B4, Cat #L2630, Sigma) over 24 hours. LPS stimulation results in the secretion of the inflammatory cytokine TNF-α by BV2 cells or PBMC, which can be quantified by ELISA in culture supernatant samples per manufacturer's protocol (Cat #558273 for BV2 and Cat #558299 for PBMC, BD Biosciences). To determine whether example compounds 1-78 inhibit TNF-α production by BV2 cells or PBMC, the cells were cultured in the presence of the compounds at different concentrations, and fold reduction in TNF-α production relative to TNF-α production by the same cells cultured in the presence of dimethylsulfoxide (as vehicle control) was determined. The results are shown in Table 2.

TABLE 2

TNF-α Inhibition.

| Ex. # | TNFα Inhibition. A = >80% inh. B = 50-80% inh. C = <50% inh. | Ex. # | TNFα Inhibition. A = >80% inh. B = 50-80% inh. C = <50% inh. | Ex. # | TNFα Inhibition. A = >80% inh. B = 50-80% inh. C = <50% inh. |
|---|---|---|---|---|---|
| 1 | A | 7 | C | 13 | B |
| 2 | A | 8 | C | 14 | C |
| 3 | C | 9 | C | 15 | C |
| 4 | B | 10 | A | 16 | C |
| 5 | A | 11 | A | 17 | C |
| 6 | B | 12 | C | 18 | C |
| 19 | C | 33 | C | 47 | C |
| 20 | C | 34 | C | 48 | C |
| 21 | A | 35 | C | 49 | A |
| 22 | C | 36 | C | 50 | A |
| 23 | B | 37 | A | 51 | A |
| 24 | A | 38 | A | 52 | C |
| 25 | C | 39 | B | 53 | C |
| 26 | C | 40 | C | 54 | A |
| 27 | C | 41 | C | 55 | A |
| 28 | C | 42 | A | 56 | A |
| 29 | A | 43 | A | 57 | A |
| 30 | C | 44 | A | 58 | A |
| 31 | A | 45 | A | 59 | C |
| 32 | A | 46 | A | 60 | A |
| 61 | A | 67 | C | 73 | C |
| 62 | A | 68 | C | 74 | A |
| 63 | A | 69 | A | 75 | A |
| 64 | A | 70 | B | 76 | A |
| 65 | C | 71 | B | 77 | A |
| 66 | C | 72 | C | 78 | C |

Microsome stability assays and Caco-2 permeability assays were performed on selected compounds of the present invention.

Microsome Stability Assay Protocol

Human liver microsomes (Corning #452117 lot 38291) or Mouse liver microsomes (Corning #452701, lot #6328004) were separately combined at a final concentration of 11.25 mg protein/compound with KxPO4 pH 7.4 (100 mM), MgCl2 (10 mM), and test compound (1 μM) and pre-incubated (10 min, 37° C.). Next, NADPH (1 mM) was added to begin reactions (total volume 100 μL). At various time points (0, 10, 20, and 40 mins), reactions were quenched with Clem stop solution (100 μL, 625 ng/mL) (C-yprotex) in Acetonitrile. Samples were centrifuged at 4000 g for 20 mins, diluted (75 μL into 75 μL 0.1% formic acid in water), and analyzed by LC-MS/MS. The results are shown in Table 3.

Caco-2 Permeability Assay Protocol

Caco-2 cells were maintained in DMEM in an atmosphere of 5% $CO_2$. For transport experiments $5 \times 10^5$ cells/well of were seeded on polycarbonate filter inserts and allowed to grow and differentiate for 21±4 days before the cell monolayers were used for experiments. Apparent permeability coefficients were determined for A→B and B→A directions with and without the presence of elacridar as a transporter inhibitor. Up to three test items and reference compounds were dissolved in Hank's balanced salt solution at pH 7.4 to yield a final concentration of 10 μM. The assays were performed in HBSS containing 25 mM HEPES (pH 7.4) at 37° C. Prior to the study, the monolayers were washed in prewarmed HBSS. At the start of the experiments prewarmed HBSS containing the test items was added to the donor side of the monolayer and HBSS without test items was added to the receiver side. Aliquots of the receiver side were taken over the 2 h incubation period; aliquots of the donor side were taken at 0 h and 2 h. Aliquots were diluted with an equal volume of methanol/water with 0.1% formic acid containing the internal standard. The mixture was analyzed by LC-MS/MS. The apparent permeability coefficients ($P_{app}$) were calculated using the formula: $P_{app}=(dC_{rec}/dt)/(A \times C_{0,donor})] \times 106$ with $dC_{rev}/dt$ being the change m concentration in the receiver compartment with time, $C_{0,donor}$ the concentration in the donor compartment at time 0, and A the area of the compartment with the cells. The results are shown in Table 3.

TABLE 3

Microsomal Stability and Caco-2 Permeability.

| Ex. # | Caco2 A → B (nm/s) | Caco2 A → B (nm/s) w/elacridar | Caco2 B → A (nm/s) | HLM ($t_{1/2}$ min) | MLM ($t_{1/2}$ min) |
|---|---|---|---|---|---|
| 1 | 16.3, 7.96 | 6.59 | 31.5 | 14 | 16.7 |
| 2 | 24.7, 22.3 | 21.5 | 57.1 | n.d. | n.d. |
| 5 | 9.86 | 8.58 | n.d. | 11.5 | 8.4 |
| 21 | 93.2 | 33.1 | n.d. | 4.2 | 3.2 |
| 42 | 0.878 | 0.408 | 1.2 | 83.8 | 110 |
| 44 | 23.6 | 20.5 | 45.4 | 42.5 | 20.6 |
| 55 | 4.27 | .693 | 9.94 | 20.6 | 21.4 |
| 56 | 0.748 | 0.849 | 1.73 | 102.7 | 23.2 |
| 57 | 11.1 | 1.3 | 8.42 | 99.2 | 46.7 |
| 58 | 21 | 8.6 | 30.9 | 6.9 | 4.7 |
| 60 | 15.8 | 9.16 | 40.7 | 14.3 | 19.8 |
| 61 | 15.5 | 10.6 | n.d | 13.6 | 23.8 |
| 63 | 0.675, 1.69, 0.675, 1.69, 2.15 | 0.336, 0.005 | 1.31 | 59.8 | 132.4 |
| 64 | 4.45, 4.45, 0.892, 0.892, 3.57 | 0.792, 0.0126 | 2.54 | 112.4 | 83.1 |
| 75 | 16 | 13.3 | 28.5 | n.d. | n.d. |
| 76 | 47.8 | 31.1 | n.d. | 25.4 | 8.3 |
| 77 | 13.3 | 0.634 | n.d. | 31.3 | 10.5 |
| 1-P | 2.18, 2.18, 0.271 | 1.05 | n.d. | 10.1 | 0 |
| 2-P | 0.532, 1.01, 1.01 | 0.282 | n.d | 0 | 0 |
| 10-P | 0.0893, 0.0893, 0.0565 | 0.0140 | n.d. | 159 | 159 |
| 14-P | 9.33, 6.35, 6.35 | 2.51 | n.d. | 25.1 | 5.5 |

Pharmacokinetic studies (mouse) were performed on the example 1, 6-P, 8-P, and 11-P compounds of the present invention. The example 1, 6-P, 8-P, and 11-P compounds were dosed in mice at 10 mg/kg p.o. (n=2). Plasma, brain, and liver were harvested at 0.5 h, 1 h, 2 h, and 4 h. The samples were analyzed by LCMS to determine levels of the example 1 compound, i.e., the active pharmaceutical ingredient (API) for prodrug examples 6-P, 8-P, and 11-P.

FIG. 1 shows the plasma levels of API for prodrug examples 6-P, 8-P, and 11-P.

Figure 2:
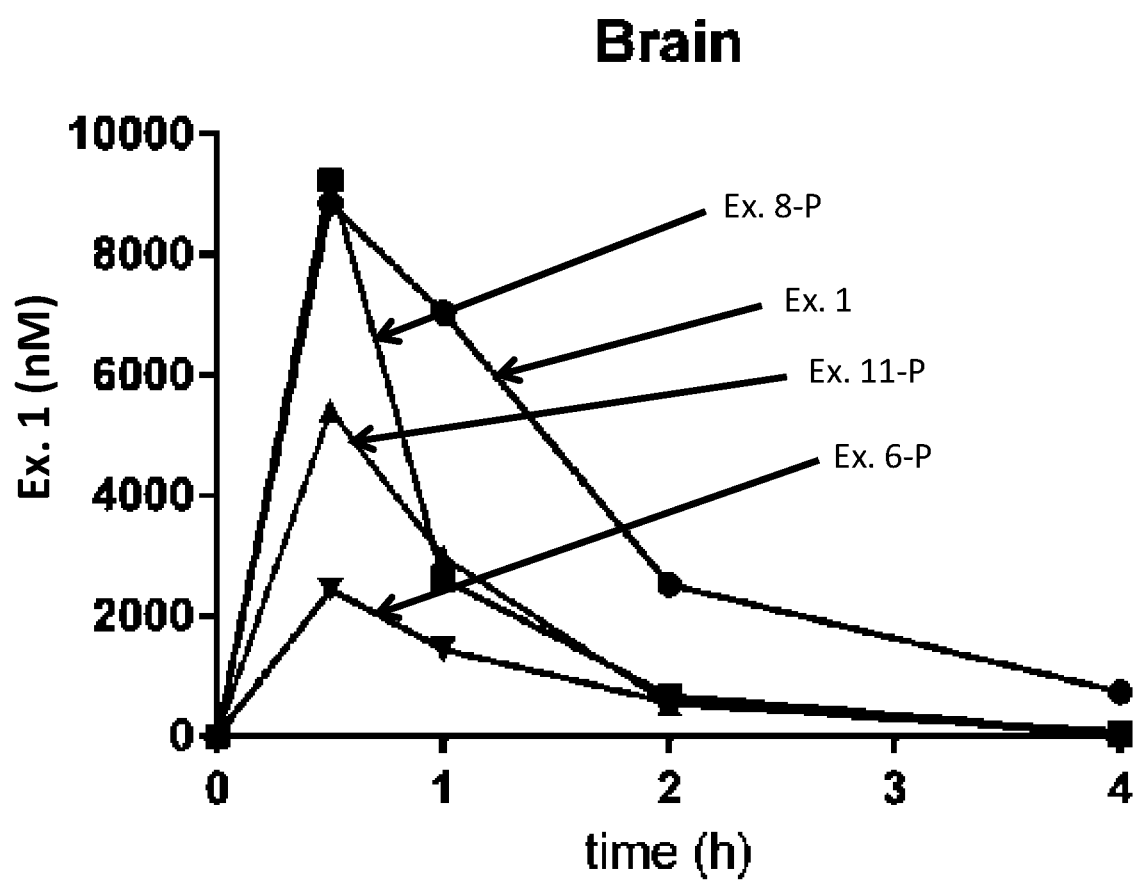
FIG. 2 shows the brain levels of API for prodrug examples 6-P, 8-P, and 11-P.

FIG. 2 shows the brain levels of API for prodrug examples 6-P, 8-P, and 11-P.

Figure 3:
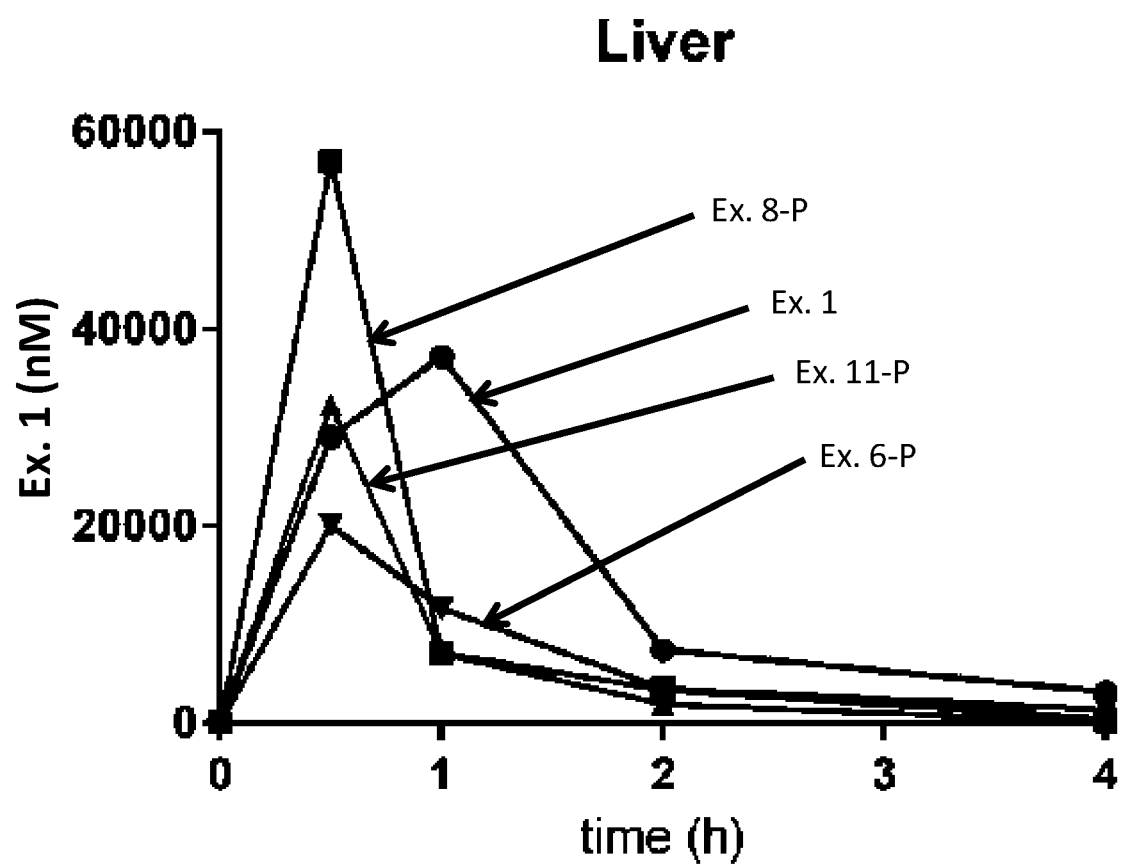
FIG. 3 shows the liver levels of API for prodrug examples 6-P, 8-P, and 11-P.

FIG. 3 shows the liver levels of API for prodrug examples 6-P, 8-P, and 11-P.

In general, FIGS. 1-3 show that prodrug examples 6-P, 8-P, and 11-P led to measurable amounts of API in plasma, brain, and liver in the mouse PK study.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

We claim:

1. A compound of formula (I):

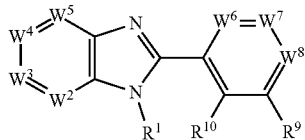

I wherein:
$W^2$ is $C-R^2$;
$W^3$ is N or $C-R^3$;
$W^4$ is N or $C-R^4$;
$W^5$ is N or $C-R^5$;
$W^6$ is CH;
$W^7$ is N or $C-R^7$;
$W^8$ is $C-R^8$;
  wherein:
    $R^1$ is $-CH_2OC(=O)R^{30}$;
      wherein:
        $R^{30}$ is chosen from
(a) $(C_1-C_6)$alkyl,
(b) phenyl substituted with (Ci-C4)alkylamino,
(c) the descarboxy residue of a natural amino acid,
(d) (Ci-C3)hydrocarbyl substituted with carboxyl,
(e) (Ci-C5)oxaalkyl, and
(f) pyridyl;
$R^2$, $R^3$, $R^4$ and $R^5$ are chosen independently from hydrogen, halogen, and perfluoro$(C_1-C_4)$alkyl;
$R^{10}$ is hydrogen;
$R^7$ is H or (C3-C4)alkyl; $R^9$ is hydrogen; and
$R^8$ is chosen from $(C_1-C_4)$alkyl, $(C_1-C_4)$alkoxy, and $NH_2$.

2. A compound according to claim 1 wherein from one to four of $W^2$, $W^3$, $W^4$ and $W^5$ are C—F.

3. A compound according to claim 1 wherein one of $W^3$ or $W^4$ is N and the other, along with $W^2$ and $W^5$, is C—H.

4. A compound according to claim 1 wherein $R^8$ is t-butyl.

5. A compound of formula (II):

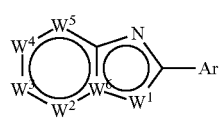

II wherein
Ar is

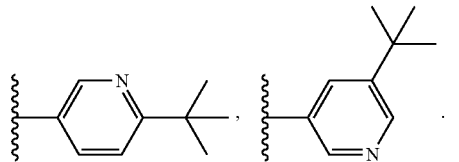

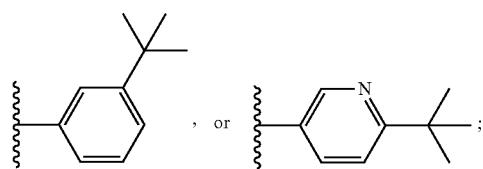 [SMILES: *c1cccc(C(C)(C)C)c1 ; "," ; "or" ; *c1ccc(C(C)(C)C)nc1 ; ";"]

$W^1$ is $N-R^1$;
$W^2$ is N or $C-R^2$;
$W^3$ is N or $C-R^3$;
$W^4$ is N or $C-R^4$;
$W^5$ is N or $C-R^5$;
$W^9$ is C;
wherein:
  $R^1$ is chosen from H, $-CH2OC(=O)R^{30}$, $-CH2OP(=O)OR^{40}OR^{41}$, $-C(=O)OR^{42}$, and $-C(=O)R^{43}$;
  wherein:
    $R^{30}$ is chosen from $(C_1-C_{10})$hydrocarbyl, $(C_1-C_{10})$hydrocarbyl substituted with amino, $(C_1-C_{10})$hydrocarbyl substituted with $(C_1-C_4)$alkoxycarbonyl, $(C_1-C_{10})$hydrocarbyl substituted with carboxyl, carboxy, $(C_1-C_6)$alkoxycarbonyl, $(C_1-C_6)$alkoxycarbonylamino, methylthio, heterocyclyl, $(C_1-C_{10})$oxaalkyl, $CHR^{44}NHR^{45}$, and guanidino;
    wherein:
      $R^{44}$ is chosen from any naturally occurring amino acid sidechain; and
      $R^{45}$ is chosen from H, methyl, and $(C_1-C_4)$alkoxycarbonyl; and
    $R^{40}$ and $R^{41}$ are chosen independently from hydrogen and $(C_1-C_6)$hydrocarbyl;
    $R^{42}$ is $(C_1-C_5)$alkyl; and
    $R^{43}$ is $(C_1-C_3)$alkyl; and
  $R^2$, $R^3$, $R^4$ and $R^5$ are chosen independently from hydrogen, deuterium, halogen, perfluoro$(C_1-C_4)$alkyl, $(C_1-C_4)$alkyl, $(C_1-C_4)$alkoxy, perfluoro$(C_1-C_4)$alkoxy, $(C_1-C_4)$acyl, $(C_1-C_4)$alkoxy$(C_1-C_4)$alkyl, hydroxy$(C_1-C_4)$alkyl, hydroxy, carboxy, $(C_1-C_4)$alkoxycarbonylamino [—HNC(=O)O-alkyl], carboxamido [—C(=O)NH2], $(C_1-C_4)$alkylaminocarbonyl [—C(=O)NH-alkyl], cyano, acetoxy, nitro, amino, $(C_1-C_4)$alkylamino, di$(C_1-C_4)$alkylamino, mercapto, $(C_1-C_4)$alkylthio, aminosulfonyl, $(C_1-C_4)$alkylsulfonyl, and $(C_1-C_4)$acylamino;
with the provision that Ar includes

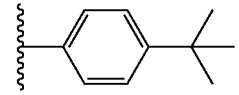

only when:

$R^1$ is not H.

6. A compound according to claim 5 wherein:

$W^2$ and $W^5$ are C—$R^2$ and C—$R^5$, respectively; and $R^2$, $R^3$, $R^4$, and $R^5$ are independently selected from H, deuterium, halo, ($C_1$-$C_3$)alkoxy, perfluoro($C_1$-$C_3$)alkoxy, nitrile, amino, hydroxyl, aminocarbonyl, ($C_1$-$C_3$)alkyl, and perfluoro($C_1$-$C_3$)alkyl.

7. A compound according to claim 5 wherein:

$R^2$, $R^3$, $R^4$, and $R^5$ are independently selected from H, halo, and perfluoro($C_1$-$C_3$)alkyl.

8. A compound according to claim 5 wherein:

$W^1$ is N—H;

$W^2$ and $W^5$ are independently chosen from C—H, C—F, C-D, C—$CF_3$, C—$CH_3$, C—Cl, C—Br, C—OH, C—$OCH_3$, C—$NH_2$, C—$CF_2$H, C—$OCF_3$, C—$OCF_2$H, C—$CD_3$, and C—$CONH_2$;

$W^3$ is chosen from N, C—H, C—$NH_2$, C—F, C—$CF_3$, C-D, C—$OCH_3$, C—CN, C—OH, C—Cl, C—$CH_3$, C—$CF_2$H, C—$OCF_3$, C—$OCF_2$H, C—$CD_3$, and C—Br; and $W^4$ is chosen from N, C—H, C—$NH_2$, C—F, C—$CF_3$, C-D, C—$OCH_3$, C—CN, C—OH, C—Cl, C—$CH_3$, C—$CF_2$H, C—$OCF_3$, C—$OCF_2$H, C—$CD_3$, and C—Br.

9. A compound according to claim 8 wherein:

$W^2$ and $W^5$ are independently chosen from C—H, C—F, C-D, C—$CF_2$H, C—$CD_3$, and C—$CF_3$;

$W^3$ is chosen from N, C—H, C—$NH_2$, C—F, C—$CF_3$, C—$CF_2$H, C—$CD_3$, and C-D;

$W^4$ is chosen from N, C—H, C—$NH_2$, C—F, C—$CF_3$, C—$CF_2$H, C—$CD_3$, and C-D.

10. A compound according to claim 5 wherein $W^2$, $W^3$, $W^4$, and $W^5$ are C—H.

11. A pharmaceutical composition comprising a pharmaceutically acceptable carrier and a compound according to claim 5.

12. The compound of formula:

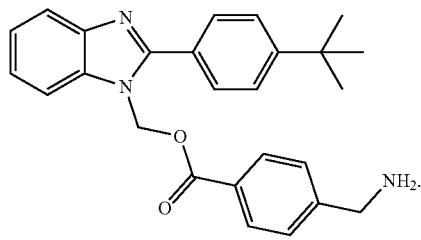 [SMILES: CC(C)(C)c1ccc(-c2nc3ccccc3n2COC(=O)c2ccc(CN)cc2)cc1]

* * * * *